United States Patent
Cohen et al.

(10) Patent No.: US 10,238,313 B2
(45) Date of Patent: *Mar. 26, 2019

(54) ELECTROMAGNETIC SENSOR FOR USE IN MEASUREMENTS ON A SUBJECT

(71) Applicant: Dune Medical Devices Ltd., Caesarea (IL)

(72) Inventors: Gil Cohen, Jerusalem (IL); Dan Hashimshony, Givat Ada (IL); Iddo Geltner, Herzlia (IL); Harel Golombek, Netanya (IL)

(73) Assignee: DUNE MEDICAL DEVICES LTD., Caesarea (IL)

(*) Notice: Subject to any disclaimer, the term of this patent is extended or adjusted under 35 U.S.C. 154(b) by 618 days.

This patent is subject to a terminal disclaimer.

(21) Appl. No.: 14/733,254

(22) Filed: Jun. 8, 2015

(65) Prior Publication Data

US 2015/0305649 A1 Oct. 29, 2015

Related U.S. Application Data

(63) Continuation of application No. 13/387,492, filed as application No. PCT/IL2010/000630 on Aug. 3, 2010, now Pat. No. 9,066,670.

(Continued)

(51) Int. Cl.
*A61B 5/05* (2006.01)
*A61B 5/053* (2006.01)
*A61B 1/313* (2006.01)

(52) U.S. Cl.
CPC .......... *A61B 5/0538* (2013.01); *A61B 1/3132* (2013.01); *A61B 2562/046* (2013.01); *A61B 2562/164* (2013.01); *A61B 2562/227* (2013.01)

(58) Field of Classification Search
CPC .... G01M 99/00; G06F 3/048; G06F 19/3481; G06F 19/3406; G06F 19/321; A61B 5/00; A61B 2562/046; A61B 2562/0233; A61B 2090/061; A61B 34/30; A61B 34/20; A61B 8/12

See application file for complete search history.

(56) References Cited

U.S. PATENT DOCUMENTS 4,955,383 A 9/1990 Faupel
5,227,730 A 7/1993 King et al.
(Continued)

FOREIGN PATENT DOCUMENTS

CN 1356546 A 7/2002
WO 9612439 A1 5/1996
(Continued)

*Primary Examiner* — Arleen M. Vazquez
*Assistant Examiner* — Brent J Andrews
(74) *Attorney, Agent, or Firm* — Browdy and Neimark, PLLC

(57) ABSTRACT

A sensor unit for use in measurements on a subject is presented. The sensor unit includes a near field electromagnetic sensor and a flexible signal transmission structure, which are integral with one another by means of at least one common continuous surface. The flexible signal transmission structure is constructed from a first layer including signal connection lines associated with sensor cells near field electromagnetic sensor and a second electrically conductive layer electrically coupled to the electrically conductive material of the sensor.

21 Claims, 17 Drawing Sheets

Related U.S. Application Data

(60) Provisional application No. 61/230,842, filed on Aug. 3, 2009.

(56) References Cited

U.S. PATENT DOCUMENTS

| | | | |
|---|---|---|---|
| 5,334,941 A | 8/1994 | King | |
| 5,573,008 A | 11/1996 | Robinson et al. | |
| 5,957,863 A | 9/1999 | Koblish et al. | |
| 6,169,254 B1 | 1/2001 | Pant et al. | |
| 6,380,747 B1 | 4/2002 | Hashimshony | |
| 6,402,689 B1 | 6/2002 | Scarantino et al. | |
| 6,411,103 B1 | 6/2002 | Tobias et al. | |
| 6,494,829 B1 | 12/2002 | New, Jr. et al. | |
| 6,546,787 B1 | 4/2003 | Schiller et al. | |
| 6,770,070 B1 | 8/2004 | Balbierz | |
| 6,813,515 B2 | 11/2004 | Hashimshony | |
| 7,087,061 B2 | 8/2006 | Chernenko et al. | |
| 7,171,252 B1 | 1/2007 | Scarantino et al. | |
| 2002/0128570 A1 | 9/2002 | Bowman et al. | |
| 2003/0187366 A1 | 10/2003 | Hashimshony | |
| 2004/0097965 A1 | 5/2004 | Gardeski et al. | |
| 2005/0021019 A1 | 1/2005 | Hashimshony et al. | |
| 2006/0004286 A1 | 1/2006 | Chang et al. | |
| 2006/0058676 A1 | 3/2006 | Yagi et al. | |
| 2006/0178699 A1 | 8/2006 | Surti | |
| 2006/0264738 A1 | 11/2006 | Hashimshony et al. | |
| 2007/0016101 A1 | 1/2007 | Feldman et al. | |
| 2007/0208271 A1 | 9/2007 | Voegele | |
| 2008/0021343 A1* | 1/2008 | Hashimshony | A61B 5/053 600/547 |
| 2008/0114354 A1* | 5/2008 | Whayne | A61B 18/14 606/49 |
| 2008/0200803 A1 | 8/2008 | Kwon et al. | |
| 2009/0062637 A1 | 3/2009 | Hashimshony et al. | |
| 2009/0253978 A1* | 10/2009 | Hashimshony | A61B 5/05 600/407 |
| 2009/0322347 A1 | 12/2009 | Hashimshony et al. | |
| 2010/0183044 A1* | 7/2010 | Tanaka | G01J 5/0011 374/128 |

FOREIGN PATENT DOCUMENTS

| | | |
|---|---|---|
| WO | 2006103665 A2 | 10/2006 |
| WO | 2007070093 A2 | 6/2007 |
| WO | 2008044012 | 4/2008 |
| WO | 2009010960 A2 | 1/2009 |
| WO | 2009156982 A2 | 12/2009 |

\* cited by examiner

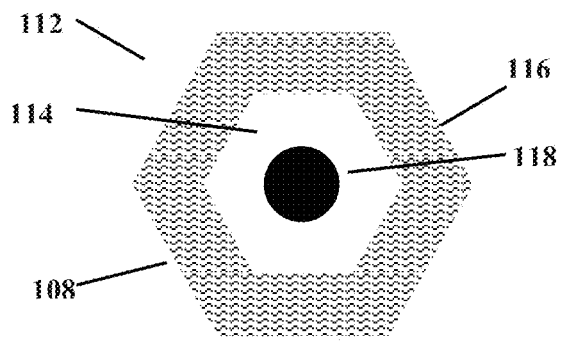
Fig. 3A
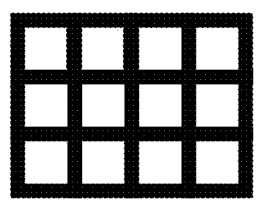    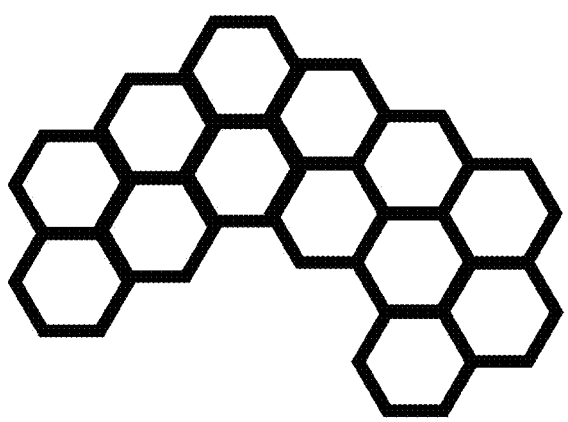
Fig. 3B             Fig. 3C
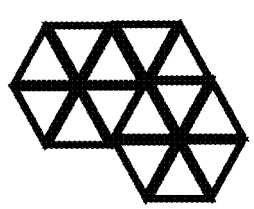
Fig. 3D

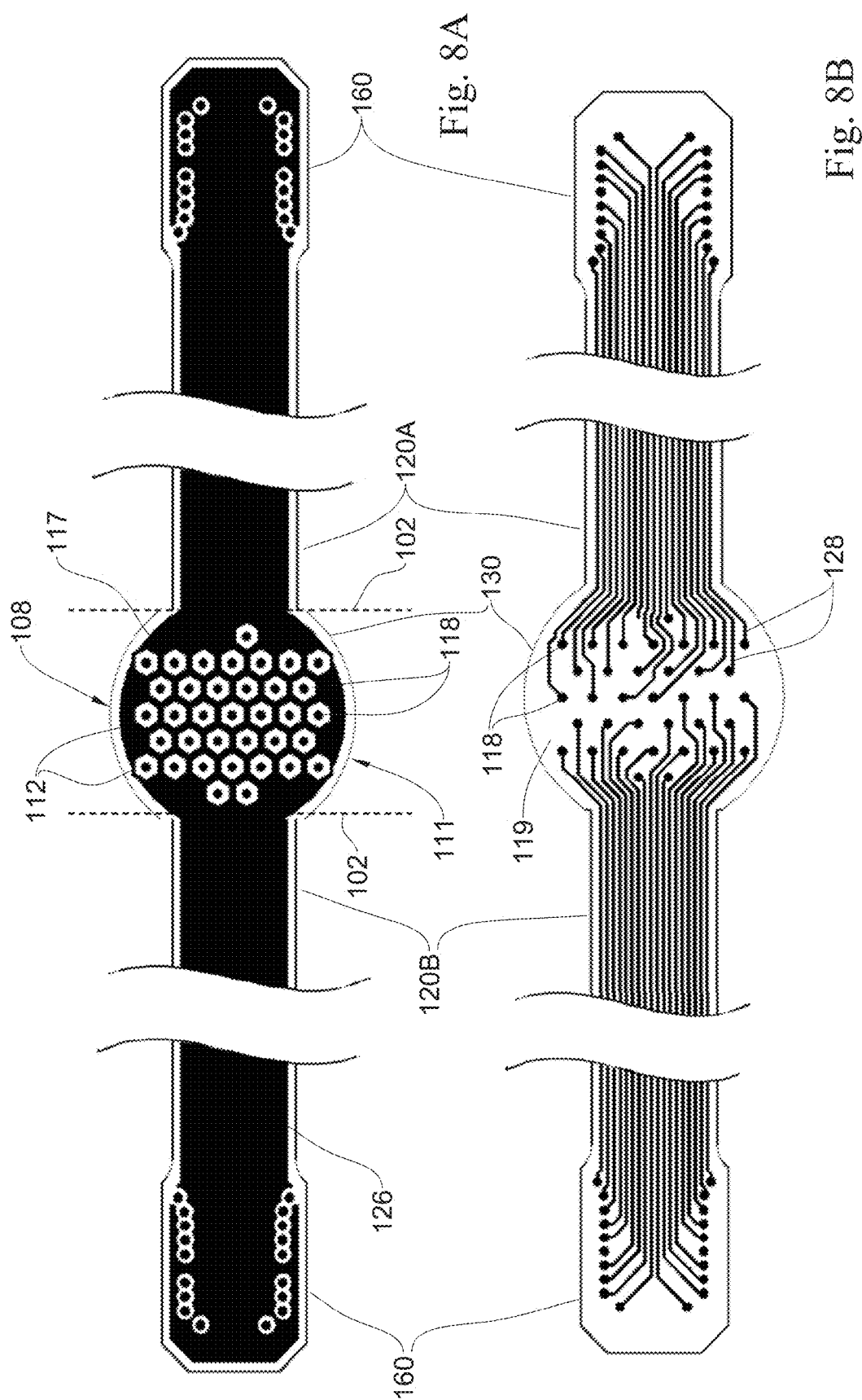

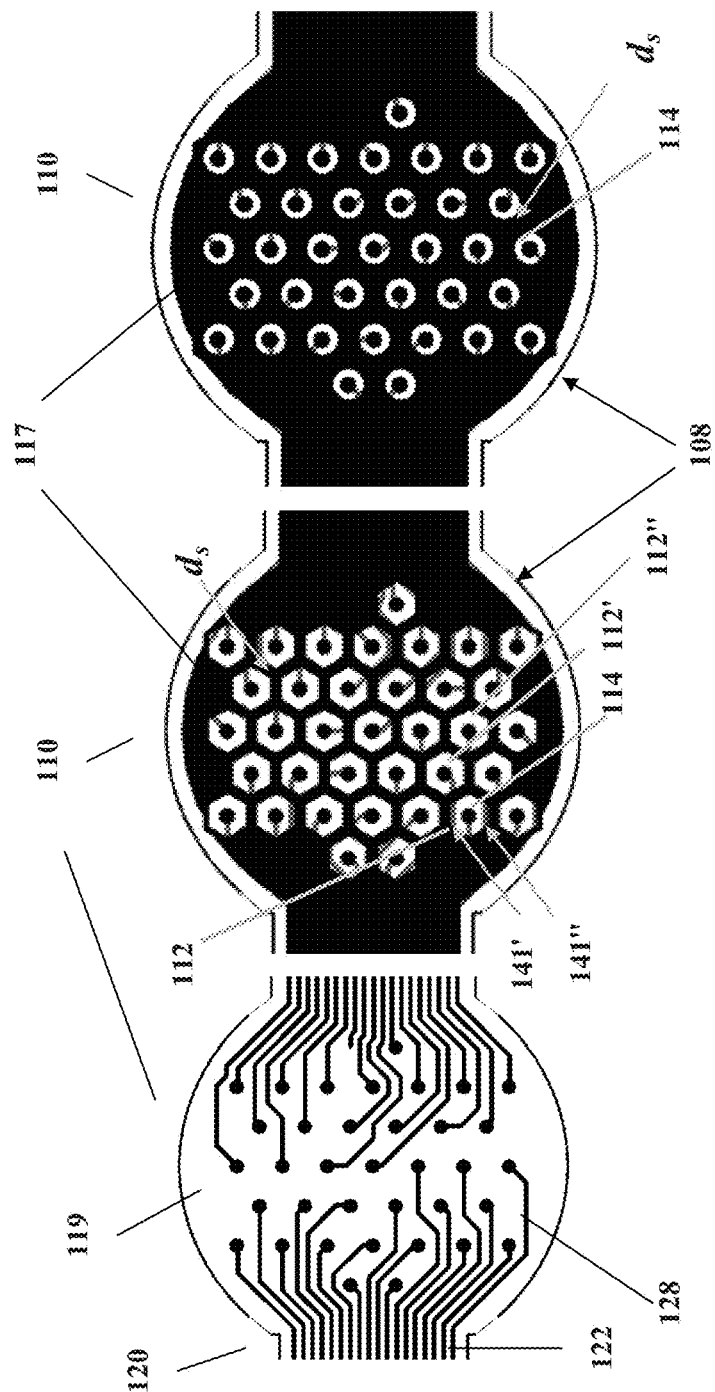

ELECTROMAGNETIC SENSOR FOR USE IN MEASUREMENTS ON A SUBJECT

FIELD OF THE INVENTION

This invention is generally in the field of medical devices, and relates to a tissue characterization sensor unit for use in measurements on a subject.

BACKGROUND OF THE INVENTION

Electromagnetic (EM) tissue characterization is a well known technique that utilizes an EM sensor to induce EM fields, of various frequency ranges, for example: constant (DC), low frequency, intermediate frequency, high frequency, radio frequency (RF) and microwave (MW) range, within a tissue and to receive therefrom EM response indicative of certain properties (e.g. dielectric properties) of the tissue portion located within a measurement region. The induced EM fields within the tissue may be near fields, or radiating fields. The EM response of the tissue might be characterized by certain EM resonance frequencies associated with the sensor-tissue coupling, or alternatively may be a broad band EM response (non-resonating) associated with the sensor-tissue coupling. Generally, the response of the tissue (or other medium/substance as the case may be) to EM fields is associated with the dielectric properties of the tissue, the response being characterized by, for example, absorbance, reflectance and/or transmittance of EM fields of different frequencies. Detection and analysis of the EM response of the tissue provides for differentiating between different tissue types.

Typically, EM tissue characterization sensors are configured as a spatial configuration of conductors that are connected with signal transmission lines, configured for carrying EM signals from an electromagnetic signal generator to the tissue to be characterized, and for carrying EM signals back from the tissue to be characterized to a signal analyzer.

For example, U.S. Pat. No. 6,813,515, assigned to the assignee of the present application, describes a probe, method and system for examining tissue, in order to differentiate it from other tissues, according to its dielectric properties. The method is of generating an electrical fringe field in the examined tissue to produce a reflected pulse therefrom with negligible radiation penetrating into the tissue itself; detecting the reflected electrical pulse; and comparing electrical characteristics of the reflected electrical pulse with respect to the applied electrical pulse to provide an indication of the dielectric properties of the examined tissue. The measuring device is built as a coaxial probe with cavity at its distal tip with respect to operator where a sample of the tissue to be examined is confined The probe itself has an inner conductor insulated from, and enclosed by, an outer conductor open at one end and extending past the inner conductor in the axial direction, defining an open cavity at the distal end of the probe with respect to the operator. The inner conductor includes a tip within the open cavity, which tip is formed with at least two different diameters for enhancing the electrical fringe field.

Some other examples of the tissue characterization sensors are described in the patent publications: U.S. Pat. Nos. 6,380,747; 5,227,730; 5,334,941; 6,411,103. Also, some sensors are exemplified in WO 06/103665 assigned to the assignee of the present application.

The use of an arrangement of multiple tissue characterization sensors is described for example in US 2008/0200803. Here, a cancer detection and treatment instrument is described. The instrument comprises: a first conductive plate; a second conductive plate which is opposed to the first conductive plate and has a first opening; a first signal line disposed between the first conductive plate and the second conductive plate; a first contact member of which one end is exposed through the first opening and of which the other end is connected to the first signal line; a dielectric portion filled between the first and second conductive plates and the first signal line; and a conductive layer surrounding both side surfaces and a front end surface of the dielectric portion which are exposed. Therefore, it is possible to accurately detect cancer by the use of the ultra high-frequency signal and to treat a diseased portion without damaging tissues around the diseased portion.

Some examples of how an array of sensors can be used for tissue characterization are described in WO 2009/010960 assigned to the assignee of the present application.

GENERAL DESCRIPTION

There is a need in the art for a novel EM tissues characterization probe having multiple sensing elements and the ability of better coupling to a tissue being measured.

It should be noted that the term "measurement" actually refers also to examination, inspection, monitoring of any parameter/condition of the tissue. The term "tissue" should also be interpreted as a general term relating also to any medium or substance, being for example a tissue of a subject and being measurable while inside or outside the subject's body (in-vivo or ex-vivo measurements).

Operation with higher number of sensing elements increases the resolution of measurements, also enabling the probe to provide sufficiently detailed pictorial/spatially resolved representation of the measured region of the medium (or tissue) under inspection. Known EM tissue characterization probes of the kind specified, namely utilizing multiple sensing elements are typically limited in a number of such sensing elements mainly because of technological limits in signal connection to and from each of the sensing elements. Further, it is often the case that better coupling between the probe and the tissue requires certain flexibility of at least a part of the probe. This requirement impose further limitation to the number of sensing elements that can be used, in particular to the number of signal connections that can be incorporated in a flexible probe.

In general, the invention may be implemented with various types of EM tissue characterization sensors, including for example electric and magnetic sensors (e.g. RF sensors), temperature, optical and chemical sensors, etc. In particular, the invention is suitable for use with any type of sensors that utilize high-frequency EM signals, i.e. require dedicated impedance controlled and, optionally, electromagnetically shielded signal transmission lines for their operation. The term "impedance controlled" refers to EM signals transferring structures (e.g. signal transmission lines) having well defined, and constant, impedance along substantially the entire extent of the structure.

More specifically, the invention may be implemented for producing pixelated tissue characterization sensor unit that is based on an array of near field electro-magnetic (EM) sensor cells. The sensor cell is a sensing element adapted to measure at least one property of a tissue to which it is coupled.

The terms near field sensing element or near EM field sensing element (e.g. sensor cell) generally refers to the sensing elements which are configured to induce near EM fields (i.e. substantially non radiating EM fields) in the inspected medium/tissue, said EM fields originating from a sensing region defined by the sensing element. Such non-radiating EM fields are typically induced by arranging the sensor conductor elements (e.g. its signal and ground conductors) such that their feature size and/or a spacing between them is significantly smaller than one wavelength of the induced EM field. Generally, also the penetration depth of a near EM field induced by such sensors is significantly smaller than one wavelength of the induced EM field, and typically it is of the order of the feature size and/or distance between the conductor elements of the EM sensor. Tissue characterization near field sensors are typically operated in high frequencies, i.e. from 100 KHz to 5 GHz (for example in the RF, MW regimes).

As indicated above, having a sensor unit including multiple sensor cells is generally advantageous since it allows to map the properties of a tissue with greater resolution and to identify more easily and accurately transition regions between different tissues for example between healthy and cancerous tissues. An EM tissue characterization sensor unit (probe) having more than a few sensor cells imposes several requirements on the configuration of both the arrangement of sensor cells and the signal feed structure (also referred to as a signal transmission structure) transmitting the EM signals to and from the sensor cells. This is because, on the one hand, the operation and measurement accuracy of many types of tissue characterization sensor cells is dependent on the coupling (e.g. attachment) of the sensor cells to the tissue. On the other hand, impedance controlled and electromagnetically shielded signal feed lines are typically cumbersome structures, and thus providing multiplicity of such feed lines to the sensor cells impairs the flexibility of the sensor unit and the ability of providing sufficient coupling between each of the sensor cells and the tissue to be inspected.

According to some aspects of the invention, a sensor unit may include a flexible signal transmission structure including multiplicity of impedance controlled and optionally also partially electrically isolated (spatially distanced from each other and/or electrically shielded) signal connection lines suitable for transmitting measurement data in the form of EM signals to and/or from the multiple sensor cells.

To this end, the flexibility and the configuration of the signal transmission structure provide several advantages, for example allowing accommodation of the sensor unit within a flexible lead (guide) such as a lumen where the flexibility of the signal transmission structure enables guiding the lumen within narrow and/or twisted pathways towards a desired region of inspection. Also, when the sensor unit is accommodated within a housing or guide, the flexibility of the connection lines allows back and forward (e.g. elastic) movement of the sensor's "head" with respect to the housing thus also enabling to control the extent by which the sensor's head protrudes from the housing/guide. The movement enables to control the degree of attachment/detachment from the inspected medium and allows protection of the sensor's head while it is not in use.

Moreover, the flexibility of the connection lines allows to achieve minimal footprint of the sensor unit by enabling to orient substantially only the sensing surface of the sensor unit in the direction of the inspection, i.e. the sensor unit when in operation faces the medium substantially only by its sensing surface. The sensing surface of a sensor unit is a surface containing multiple sensing regions of multiple sensor elements or sensor cells, where the sensing regions are arranged in a spaced-apart relationship. In this connection, it should be understood that generally a sensing region is not limited to a planar region but rather is typically a volumetric region. Hence, sensing surface is a physical surface of the sensor unit intersected by all the sensing regions. Such reduction of the footprint can be achieved by enabling bending of the flexible signal transmission structure (e.g. in 90°) at the vicinity of the boundary between the signal transmission structure and the sensor (e.g. the sensor's sensing surface). Thus, the surface of the sensor unit by which it is coupled to a region of interest in the medium is of a size close to the size of the active region of the sensing surface occupied by the multiple sensing regions. A region of interest is actually a volume of the medium which is probed, or interrogated, by the sensor unit. This volume is defined by the sensing surface and by the penetration depth of the near field into the medium (which is set by the structure of the near filed of the sensing cell). It should be understood that the region of interest of a subject is defined per a measurement site.

It should be noted that in some types of tissue characterization sensors (e.g. such as EM sensors configured to induce near EM fields that extend from the sensor's sensing surface into proximate regions of a tissue coupled thereto), good coupling between the sensor sensing surface and the tissue, without gaps (e.g. air gaps) between them, provides more accurate and stable tissue characterization measurements. Hence, according to some embodiments of the invention, sufficient coupling between the sensor cells (e.g. and thus coupling the sensor, including the sensing surface) and the inspected tissue/medium is obtained by configuring the sensor as a flexible structure that allows firm attachment of the sensing surface, and the sensing regions thereon (which are associated with the sensor cells), to the tissue.

It should, however, be understood that some types of sensors such as radioactive field sensors or far EM field (radiating) sensors can be operated with or without direct contact with the tissue or with less sensitivity to the degree of attachment with the tissue. In some embodiments of the present invention, the sensor unit is made in the form utilizing flexible circuit techniques such that all the elements of the sensor unit (e.g. the sensor's head and the signal transmission structure) are flexible while in other embodiments certain parts such as the sensor's head and or connector elements are rigid and the sensor unit is fabricated by utilizing rigid-flexible circuit techniques. A flexible sensor head is advantageous for analyzing/examining/probing/querying/investigating the EM properties (dielectric properties) of a non-planar substance surface, and for dynamic conforming of the sensor surface to an examined substance surface.

Flexible or Rigid-Flexible circuits (also known as flex-based circuits) are typically manufactured by patterning arrangements of printed conductor configurations (electrical traces) on a base material (i.e. known as the flexible laminate material) with or without flexible cover layers. In general, flexible circuits are produced in methods which are generally parallel to those of printed circuit board constructions. These include, for example, single-sided flexible circuits, double-sided flexible circuits, multilayer flexible circuits (having three or more conductor layers), combinations of flex and rigid circuits, and flex-rigid circuits. As flexible laminate material is generally either single sided or double sided metal clad, when multilayer flexible circuits are manufactured, the layers of the circuit are bonded by bondply or sheet adhesive and electrical connections between the layers are generally made by plated-through holes interconnections.

The following are some examples of the flexible circuit base materials, also known as flexible metal clad dielectrics or flexible laminate materials, which might be used in the fabrication of the sensor unit of the present invention: Pyralux AP 8535R Adhesiveless double side copper clad polyamide (Kapton) by Dupont company; UPISEL-N BR 1120 Adhesiveless double side copper clad polyamide by UBE company; Pyralux AC 181200R Adhesiveless single side copper clad polyamide by Dupont company; UPISEL-N SR 1220 Adhesiveless single side copper clad polyamide by UBE company; Pyralux LF 7011R Adhesive bonded double side copper clad polyamide by Dupont company; Pyralux LF 7041R Adhesive bonded single side copper clad polyamide by Dupont company; Pyralux LF 0230 polyamide coverlay by Dupont company; Pyralux FR 0131 polyamide bondply by Dupont company; Pyralux LF 0300 sheet adhesive by Dupont company. It should be noted that other suitable materials can be used in the invention as well.

The requirement for flexibility of the signal transmission structure generally leads to, or results in, the construction of this structure, incorporating the minimal number of conductive layers and a minimal spacing between these conductive layers. This type of construction imposes restrictions on the configuration of signal lines within the sensor, the sensor being integral with the signal transmission structure.

Since the high frequency signals are susceptible to EM interferences, it is preferable to electrically isolate signal lines associated with different sensor cells from each other to prevent a cross talk between the different cells. Although this may generally be achieved by passing the signal line(s) towards and away from a specific sensor cell along a path outside of other cells, such a solution would require certain minimal separation between the sensor cells to accommodate a path for the signal lines, thus reducing the fill factor of sensing regions (formed by a plurality of the sensor cells) within a sensing surface of the probe. Also, increase in the number of sensor cells (e.g. per unit area in order to provide higher spatial resolution or in order to enlarge the sensing area), generally requires passing a greater number of signal lines. This is generally achieved by either further increasing the separation/spacing between the sensor cells within a sensing surface and reducing the fill factor of the sensor unit, or by increasing the number of signal lines per unit area (signal line density) thus affecting the interference and cross talk between the lines.

However, in accordance with some embodiments of the present invention, a sensor unit having high number of sensor cells (e.g. arranged with high spatial resolution) is implemented without impairing or restricting either one of the fill factor of the sensor or its signal to noise ratio (SNR). This is achieved, as is further exemplified below, by allowing the signal lines associated with sensor cells to traverse "beneath" and across the sensing regions of other sensor cells while being electromagnetically shielded from said sensing regions. In other words, the signal line can be arranged such that its projection onto the sensing surface intersects the sensing region. This allows to maintain both the sufficient spacing between the signal lines (e.g. providing good electromagnetically isolation) and the minimal spacing between the sensing regions of the sensor cells, allowing high fill factor. Hence, preferably, the multiple signal lines associated with the sensor cells are configured to increase SNR of the sensor unit by reducing/minimizing interferences caused for example by a cross talk between the signal lines.

A tissue characterization probe of the present invention includes a sensor unit includes multiple spaced-apart sensing regions located in a sensing surface and associated respectively with an array of multiple sensor cells. The sensing surface may contain a relatively large number of sensing regions for example more than 5 sensing regions and preferably more than 35 sensing regions. Additionally or alternatively, the sensing surface may be characterized by a desirably high resolution, for example more than 5 sensing regions per 35 $mm^2$ area and preferably more than 35 sensing regions per 35 $mm^2$ area. The sensing surface may be characterized by high fill factor of the sensing regions arranged in a spaced-apart relationship such that the area of the spaces between the sensing regions does not exceeds 50% from the area of the sensing regions, preferably not exceeding the 10% of said area. The size of the sensing surface ranges from about 1 mm to 10 cm. The size of the sensing region of the sensor cell (the projection of the sensing region onto the sensing surface) ranges from about 0.5 mm to about 5 mm. This parameter defines the upper limit of a range of the minimal feature size detectable by the sensor unit.

According to one broad aspect of the invention, there is provided a sensor unit for use in measurements on a subject. The sensor unit comprises a near field electromagnetic sensor, and a flexible signal transmission structure. The sensor comprises a sensing surface by which the device faces a region of interest of the subject, and an array of sensor cells each configured to define a sensing region surrounded by an electrically conductive material, an array of the sensing regions being arranged in a spaced-apart relationship within said sensing surface. The flexible signal transmission structure is integral with the near field electromagnetic sensor such that the signal transmission structure and the near field electromagnetic sensor have at least one common continuous surface. The flexible signal transmission structure comprises: a first layer including an array of signal connection lines associated with the sensor cells (e.g. being electrically connected/coupled, directly or not, to respective elements of the sensor cells), and a second electrically conductive layer electrically coupled to said electrically conductive material of the sensor.

The signal transmission structure and the near field EM sensor may be configured for providing impedance controlled signal transmission along to and from the sensing regions.

Preferably, each of at least some of the sensor cells comprises an inner conductor element coupled to the inside of the respective sensing region and electrically coupled to the respective one of the signal connection lines. Thus, the signal connection lines are associated with the sensor cells by electrical connection/coupling of the signal transmission lines to the inner conductor elements of the sensor cells. At least some of the sensor cells may be configured as a resistive type sensor (comprising the inner conductor element electrically insulated from the surrounding electrically conductive material, with or without an electrical insulator material covering the sensing region) or inductive type sensors (the sensing cells being connected to the electrically conductive material surrounding the respective sensing region).

Preferably, the flexible signal transmitting structure has at least one flexible band configured for bending with respect to the sensor with a radius of curvature smaller than a characteristic dimension of said sensor. Such bending and flexibility of the band(s) allow for reducing the footprint of the sensor unit (i.e. the size of its surface by which it is coupled to the tissue) and also for enabling repetitive movement of the sensor unit with respect to its housing.

In some embodiments of the invention, the sensor is configured as a multi-layer structure, e.g. comprises first and second sensor layers. The first sensor layer comprises a plurality of signal lines, which are electrically coupled to the signal connection lines of the signal transmission structure (the signal connection lines are thus associated with the corresponding sensor cells). The second sensor layer comprises said electrically conductive material and defines the sensing surface of the sensor unit. The second sensor layer is electrically coupled to the second electrically conductive layer of the signal transmission structure. Considering the sensor cells' configuration with the inner conductor elements, the signal connection lines of the signal transmission structure are electrically coupled to the inner conductor elements of the sensor cells via the signal connection lines of the sensor.

In some embodiments, the signal lines (at least some of them) are associated with the respective sensing regions and extend in the first sensor layer along respective paths, such that a projection of each of these paths onto the sensing surface is located outside all other sensing regions. In some other embodiments, the signal lines extend in the first sensor layer along respective paths, such that a projection of each of these paths onto said sensing surface intersect with one or more of the other sensing regions.

The sensor unit may be configured with an additional electrically conductive sensor layer located within the sensor in between the first and second sensor layers. This additional conductive sensor layer has spaced-apart signal transmission regions configured as substantially non-conductive regions aligned with at least some of the sensing regions. The signal transmission regions are substantially smaller than the corresponding sensing regions, thereby providing by said additional conductive sensor layer an electrical screening of at least a portion of the signal lines from the sensing regions.

The additional conductive sensor layer may be configured to provide electrical screening of the signal lines extending along paths the projections of which onto said sensing surface intersect one or more of the sensing regions.

In some embodiments, at least some of the signal lines of the first sensor layer terminate within at least some of the sensing regions associated therewith. The signal lines are connected, at their termination within the sensing regions, with the inner conductor element protruding from the first sensor layer towards the sensing surface, such that the electrically conductor elements induce electromagnetic field profile extending outwards from the sensing surface through said sensing regions.

As indicated above, the signal transmission structure preferably comprises one or more flexible bands capable of bending with respect to the sensor. Such one or more bands may extend from the sensor along one or more directions.

In some embodiments, at least one of the sensor cells is configured and operable as a reference cell. Such reference cell is configured to be substantially insensitive to effects of a region of interest of the subject to which the sensor is coupled during operation.

Preferably, the signal transmission structure is configured as a flexible planar microstrip having a plurality of layers including the first and second layers being flexible planar layers. Alternatively, or additionally, the signal transmission structure may be configured as a flexible planar strip comprising a plurality of layers including the first and second layers, and additional electrically conductive layer, where the first layer is enclosed between the second and the additional layers.

According to another broad aspect of the invention, there is provided a sensor unit for use in measurements on a subject, the sensor unit comprising: a near field electromagnetic sensor comprising a sensing surface by which the device faces a region of interest of the subject, an array of sensor cells each configured to define a sensing region surrounded by an electrically conductive material, an array of the sensing regions being arranged in a spaced-apart relationship within said sensing surface; and a flexible signal transmission structure integral with said near field electromagnetic sensor such that the signal transmission structure and the near field electromagnetic sensor have at least one common continuous surface, said flexible signal transmitting structure having at least one flexible band configured for bending with respect to the sensor with a radius of curvature smaller than a characteristic dimension of said sensor.

According to yet another broad aspect of the invention, there is provided a sensor unit for use in measurements on a subject, the sensor unit comprising:

a near field electromagnetic sensor comprising an array of sensor cells each comprising a sensing region and an inner conductor element located within said sensing region, the sensing regions of the sensor cells being arranged in a spaced-apart relationship within a sensing surface; and a flexible signal transmission structure integral with said near field electromagnetic sensor, said flexible signal transmission structure comprising a first layer including signal connection lines electrically coupled to the inner conductor elements respectively.

According to yet further aspect of the invention, there is provided a sensor unit for use in measurements on a subject, the sensor unit comprising:

a near field electromagnetic sensor comprising a sensing surface by which the device faces a region of interest of the subject, an array of sensor cells each defining a sensing region surrounded by an electrically conductive material and comprising an inner conductor element coupled to the inside of the sensing region, an array of the sensing regions being arranged in a spaced-apart relationship within said sensing surface; and a flexible microstrip which is integral with said near field electromagnetic sensor and is capable of bending with respect to the sensor, said flexible microstrip comprising a first conductive layer being an extension of said electrically conductive material and a second conductive layer carrying an array of signal connection lines electrically coupled to said inner conductor elements.

In yet another broad aspect of the invention, there is provided a sensor unit for use in measurements on a subject, the sensor unit comprising:

a near field electromagnetic sensor comprising an array of sensor cells each comprising a sensing region and an inner conductor element located within said sensing region, the sensing regions of the sensor cells being arranged in a spaced-apart relationship within a sensing surface; and a flexible signal transmission structure integral with said near field electromagnetic sensor, said flexible signal transmission structure comprising a first layer including signal connection lines electrically coupled to the inner conductor elements respectively.

The invention also provides a sensing device comprising one or more of the above-described sensor units.

Also, the invention provides a novel measurement device for use in measurements on a subject, where the measurement device comprises: the above-mentioned sensing device, and a calibration and probe control unit (CPC) which is integral with said sensing device and which is configured for connecting to a network analyzer. The CPC preferably comprises a number of terminals associated with a plurality of calibration loads of known RF reflection coefficients respectively and comprises a memory utility carrying recorded data indicative of the RF reflection coefficients and recorded data indicative of RF transfer coefficients of the CPC unit, thereby enabling calculation of the RF response of each of the sensor cells within the sensing surface of the sensor unit, while remaining the sensor unit integral with CPC unit.

BRIEF DESCRIPTION OF THE DRAWINGS

In order to understand the invention and to see how it may be carried out in practice, embodiments of the invention will now be described, by way of non-limiting examples only, with reference to the accompanying drawings, in which:

FIGS. 3A to 3J show examples of the configuration of a sensor cell and arrangement of cells suitable for use in the sensor unit of the present invention, where FIGS. 3A, 3C, 3E, 3F 3H and 3J exemplify sensor cells having a hexagonal geometry of the sensing region contour, FIGS. 3B, 3G and 3I exemplify sensor cells having a rectangular geometry of the sensing regions, and FIG. 3D exemplifies sensor cells having a triangular geometry of the sensing regions; FIGS. 3A, 3E and 3F exemplify sensor cells having inner conductor elements of a circular cross-section at the distal end, and FIGS. 3G-3J show sensor cells having various other geometries of the cross-section at the distal end of the inner conductor elements; FIGS. 3A, 3E-3G show sensor cells in which the inner conductor element is electrically insulated from the contour of the respective sensing region and FIGS. 3H-3J show sensor cells having their inner conductor element electrically connected to the contours of the respective sensing regions;

FIG. 5A shows a strip planar structure, and FIG. 5B shows a micro strip planar structure;

FIGS. 8A to 8C show different cross-sectional views of a sensor unit according to yet another example of the invention;

FIG. 9A-9D exemplify a relation between the signal lines and sensing regions in the sensor unit according to the invention, where FIG. 9A shows a signal layer of the sensor, FIGS. 9B and 9C show two examples of different configurations of the conduction layer providing respectively high fill factor of the sensing regions, and high SNR with reduced crosstalk; and FIG. 9D shows an enlarged view of a portion of the configuration of FIG. 9B;

DETAILED DESCRIPTION OF EXEMPLARY EMBODIMENTS

Figure 1A:
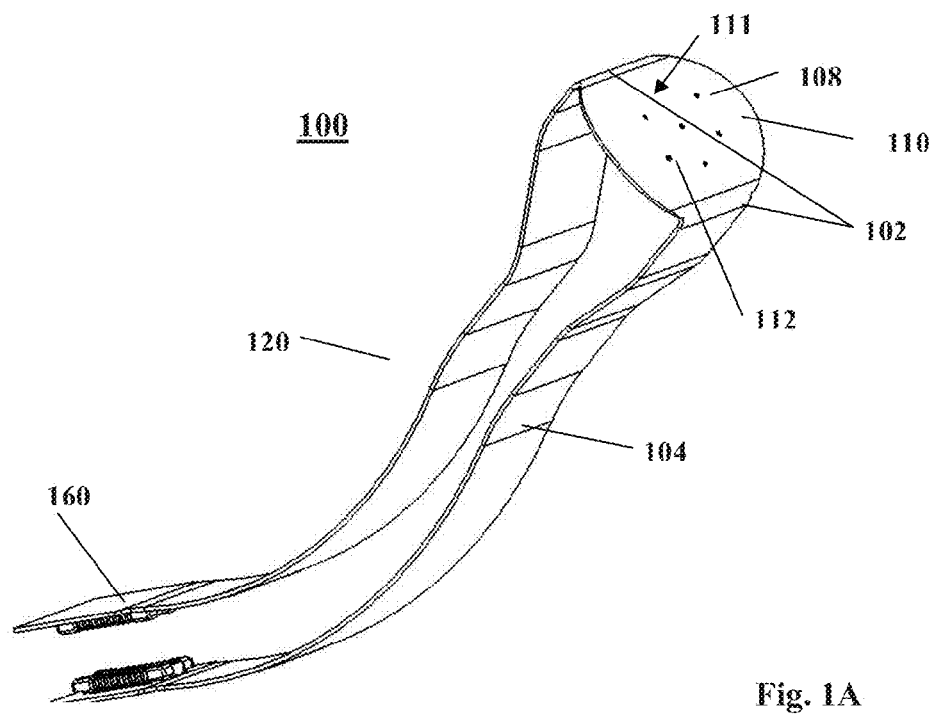
FIGS. 1A and 1B show a schematic illustration of an example of a sensor unit, shown respectively before and after assembling the sensor unit on a fixture.
Figure 1B:
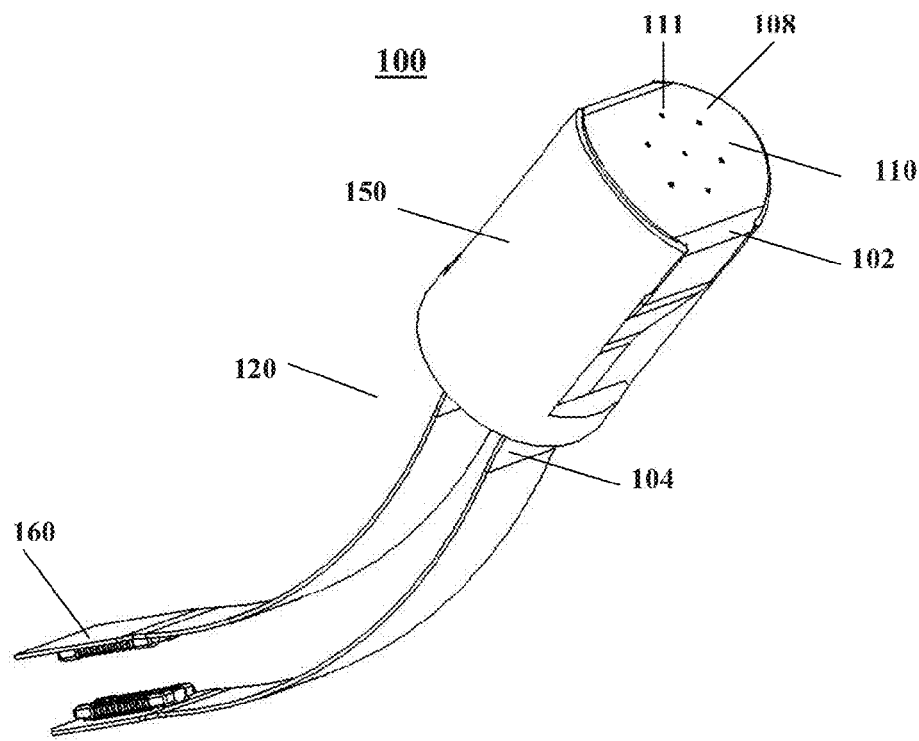

Reference is made to FIGS. 1A and 1B illustrating schematically a sensor unit 100 according to an embodiment of the present invention. In these figures, the sensor unit 100 is shown respectively before and after assembling the unit on a fixture 150. Sensor unit 100 includes an integral structure including a sensor or sensor head 110 and a flexible signal transmission structure 120. The configuration is such that the sensor and the signal transmission structure have at least one common continuous surface. Also, both the sensor and the signal transmission structure are substantially flat. As also exemplified in the figures, an appropriate signal connector structure 160 is provided for electrically connecting signal transmission structure 120 to a control unit/signal generator/signal analyzer (not shown here).

In this example, sensor unit 100 is configured for tissue characterization, by providing data indicative of the type of the inspected tissues and/or indicative of boundaries and transitions between different tissue types along the sensing surface 108. Sensor 110 includes a plurality 111 of sensor cells 112 arranged in a spaced-apart relationship within a sensing surface 108. The sensor cells are appropriately distributed within/spanned across the sensing surface, e.g. tiling or covering the sensing surface 108. Each sensor cell is operable to inspect/measure/characterize/examine/probe/query/investigate at least one characteristic/parameter of a tissue to which the sensing region is coupled (either by direct contact or by proximity to the tissue).

Figure 11:
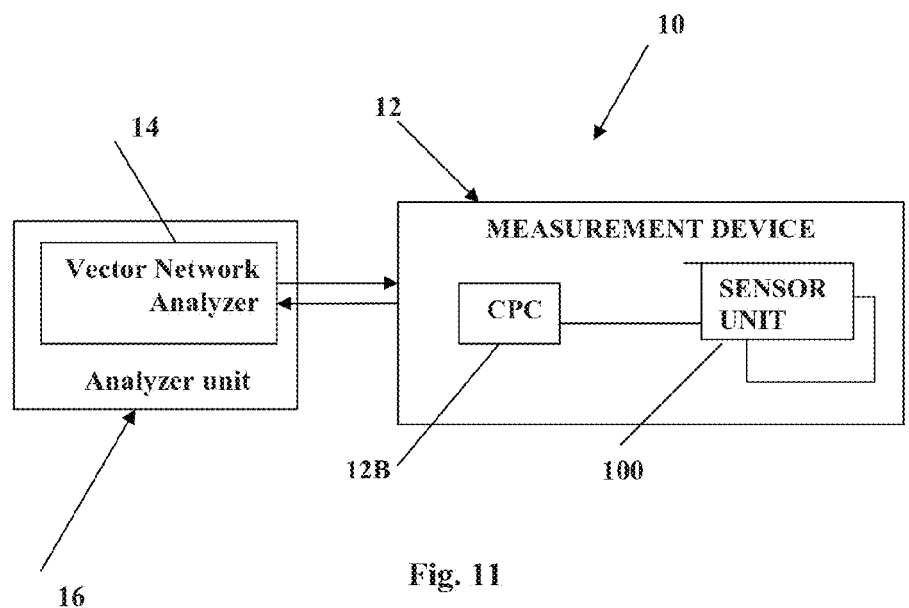
FIG. 11 is a block diagram of a measurement system comprising a measurement device utilizing sensor unit(s) of the present invention integral with a calibration and probe control (CPC) unit.

It should be noted that the sensor unit can be associated with an appropriate calibration system, including a calibration unit connectable to a network analyzer. This is schematically illustrated in FIG. 11, showing, by way of a block diagram, a measurement system, generally designated 10. The system 10 includes a measurement device 12 connectable to an analyzer 16. The measurement device 12 of the present invention includes one or more sensor units 100 and a calibration and probe control (CPC) unit 12B. The analyzer 16 includes a network analyzer 14, and also a suitable communication unit (not shown) for handling digital and/or analog communication with the CPC unit 12B.

The network analyzer 14 may be of any known suitable type and therefore need not be described in details, except to note that it is configured and operable for transmitting and receiving RF signals. Network analyzer 14 may be configured and operable as a vector network analyzer (VNA), for recording both the relative amplitude and the phase of RF signals. Network analyzer 14 is configured for carrying out the following: transmitting and receiving RF signals via its signal ports; analyzing the received signals to determine the amplitude and, optionally, phase thereof which are indicative of the signal interaction with calibration loads; and delivering the calibration correction parameters. Network analyzer 14 is also configured for measuring an RF response of the measurement device 12 using the calibration correction parameters. The analyzer 16 may have additional features, for example may be responsible for security issues to prevent reuse of the measurement device 12 or installation of other non-authorized measurement device in the system. Analyzer 16 may also provide at least one of the following facilities to measurement device 12: electrical power supply, means for handling digital and/or analog communication with measurement device 12, vacuum/pressure communication 19, a liquid dispensing line, optical signal communication, ultrasound signal communication, as well as provide control and power to an ablative/cutting apparatus/tool in measurement device 12, user and/or machine input and/or output, and control of other types of probes to be used in measurement device 12.

Figure 12A:
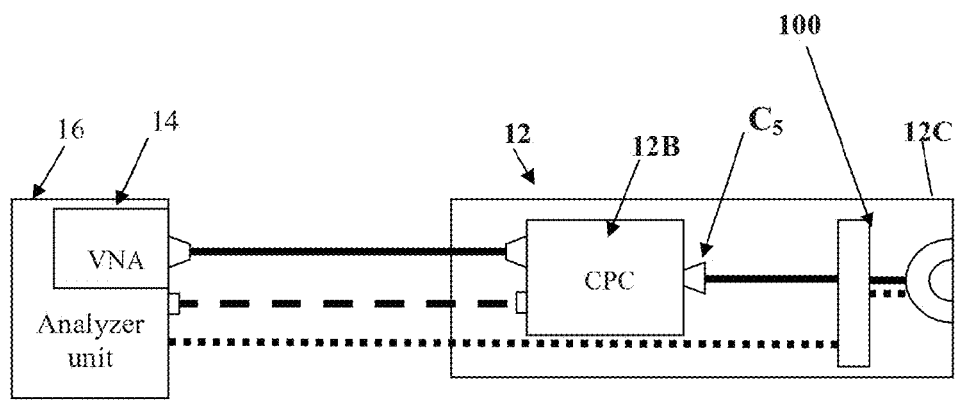
FIGS. 12A and 12B more specifically exemplify the configuration of the measurement device of FIG. 11.
Figure 12B:
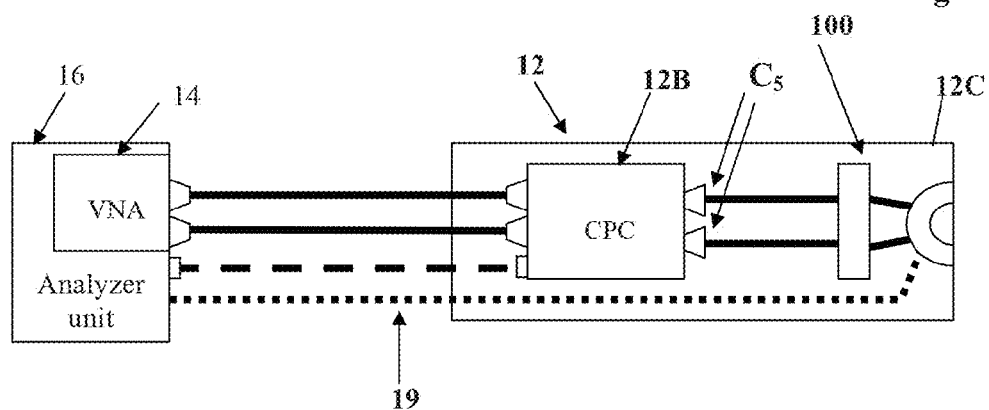

FIGS. 12A and 12B show specific but not limiting examples of the configuration of the measurement system 10. The measurement device 12 includes a sensor unit 100 and a CPC 12B integral with the sensor unit 100, which are accommodated in a common housing 12C. The sensor unit 100 is connected to the CPC 12B via a cable with an appropriate connector. In the example of FIG. 2A, there is only one RF signal connection (RF port connection) between the analyzer 16 and the measurement device 12. In the example of FIG. 2B, there are two RF signal connections (RF port connections) between the analyzer 16 and the measurement device 12. As shown in the figure, a vacuum/pressure communication line may be used for providing vacuum/pressure communication 19 to the sensor unit 100.

It should be appreciated that embodiments of the present invention may utilize more than two RF signal connections between analyzer 16 and measurement device 12. There may generally be n such RF signal connections (RF port connections) between the analyzer unit and measurement device, n being an integer equal to or greater than 1.

The CPC unit 12B is connected to the sensor unit 100 via an RF grade connector $C_5$ (for example SMA). Turning back to FIGS. 1A and 1B, the signal connector structure 160 may be configured as the RF grade connector to provide an interface that can define a calibration plain and give repeatable measurement results.

The CPC unit 12B includes a number of terminals associated with a plurality of calibration loads of known RF reflection coefficients respectively and includes a memory utility. The latter carries recorded data indicative of the RF reflection coefficients and recorded data indicative of RF transfer coefficients of the CPC unit. This configuration enables calculation of the RF response of each of the sensor cells within the sensing surface of the sensor unit, while remaining the sensor unit integral with CPC unit. It should be understood that the CPC may also be used for selectively directing EM signals to one or more sensor cells.

Preferably, the CPC unit 12B (implemented as a printed circuit board) is enclosed within a housing, having an RF cover, to provide mechanical strength and electromagnetic immunity to the CPC unit 12B. Mechanical strength of the housing enables better calibration by eliminating geometrical distortion, which may occur, for example, due to mechanical stresses or environmental changes of the CPC unit. This distortion may result in changes in the propagation of RF signals within the CPC unit, leading to degradation in calibration performance. Electromagnetic immunity of the housing enables better calibration by reducing RF interference of the CPC unit 12B with the sensor unit 100, and by reducing RF interference of external RF sources with the CPC unit 12B. Connectors of CPC unit 12B may be integrated into the housing. Housing may be constructed to enable operation of measurement device 12 in various environmental conditions, and to enable sterilization of the measurement device, by use of radiation and/or gas.

The calibration unit 12B can generally have any suitable configuration, preferably either one of those disclosed in the co-pending International application PCT/IL2009/000611, assigned to the assignee of the present application, and which is incorporated herein by reference.

It should be understood that multiple sensor cells enable to spatially map properties of a medium or tissue facing the sensing surface, with spatial coverage and resolution according to the number and size of the sensor cells. Also, the size of the sensor cells determines the feature detection size of the sensor 110 as each sensor cell integrates over the value of the properties of the medium within (e.g. beneath) the sensing region of the sensor cell. Hence, such spatial mapping may provide pictorial view of the spatial distribution of values of different tissue parameters measured by the sensor cells with certain minimal feature size corresponding to the areas of the cells' sensing regions. Such a pictorial view of a medium or tissue facing the sensing surface may also be regarded as a pictorial representation, spatial representation, spatial resolved detail/spatial resolved presentation/spatial resolved description/spatial resolved depiction. It should be understood that the sensors cells may be of the same type (e.g. measuring/inspecting the same parameters of the tissue) or of different types. The sensor cell types may include inter alia radio frequency (RF) and/or micro wave (MW) sensors, as well as one or more of other electric and magnetic sensors.

More particularly in the present example, sensor 110 is configured and operable as a near-field EM sensor including array 111 of near field EM sensor cells 112 that are configured to induce, within tissue regions located proximate to the sensor's sensing surface, near EM fields corresponding to signals transmitted to this tissue region from a signal generator. The configuration and strength of the induced fields, per specific sensor structure (specific arrangement/configuration and types of sensor cells), depend on the dielectric properties of the tissue regions adjacent/in close proximity to the sensor's sensing surface. Some examples of the configuration of the sensor cell and the multiple-cell arrangement will be described further below.

In the example of FIGS. 1A and 1B, the integral sensor unit 100 is fabricated by the so-called flexible or rigid-flexible circuit techniques that allow conduction of multiple signal lines to and from the sensor 110 in a substantially flat and elastic arrangement thus providing flexibility of certain parts/regions of the sensor unit. In particular, flexibility of regions 102 of the signal transmission structure 120 near its boundary with the sensor 110 (sensor head) allows to wrap the signal transmission structure 120 (e.g. about the fixture 150) with a tight (small) bending radius. This allows for reducing a footprint of the sensor unit. Also, flexibility of some other regions of sensor unit 100, such as regions 104 of signal transmission structure 120, provides for repetitive, repeatable, elastic movement of the sensor's head 110 with respect to its connectors 160, thus allowing relative movement of the sensor with respect to a housing or guide (not shown) in which the sensor might be accommodated. It should be noted that the technique of the present invention while utilizing the flexibility of the transmission structure of the sensor still enables passage therethrough of a plurality of high frequency signal transmission lines to the sensor 110.

Figure 2:
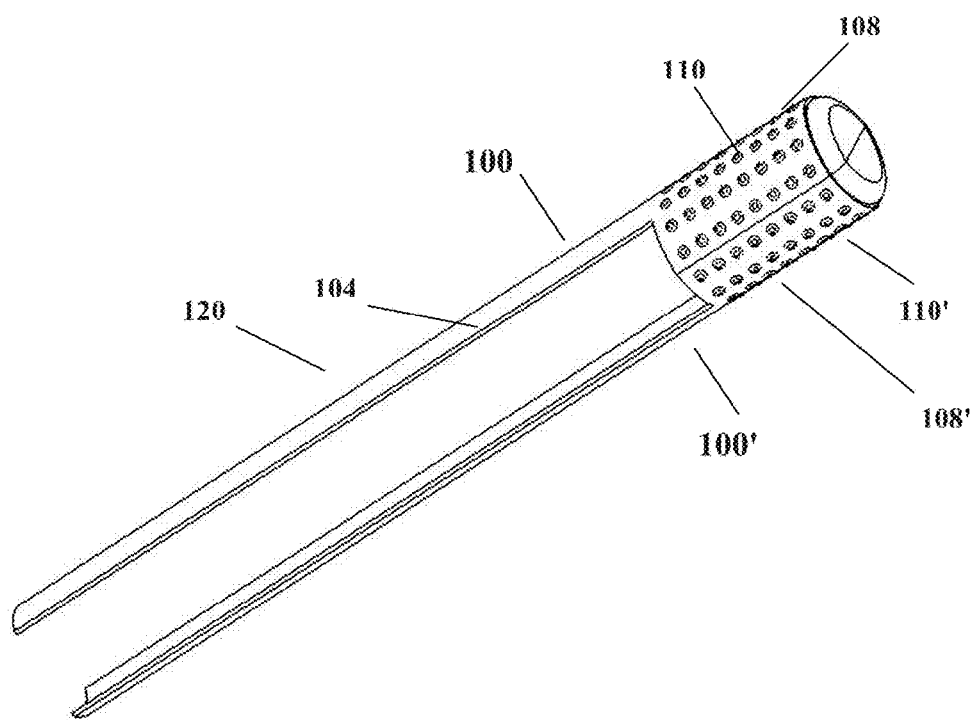
FIG. 2 is a schematic illustration of a sensing device according to another example of the invention, where the sensing device is formed by two sensor units generally similar to that of FIGS. 1A-1B.

Referring now to FIG. 2 there is illustrated schematically a sensing device utilizing the principles of the invention. Here, the device is formed by two sensor units 100 and 100' configured generally similar to the sensor illustrated in FIGS. 1A and 1B but being of different geometries. In order to facilitate understanding of the invention, the same reference numerals are used to designate elements common in all the examples of the invention. The two sensor units 100 and 100' are similar, each including a sensor (110, 110') and a flexible signal transmission structure (120, 120'), and are geometrically complementary defining together a two-part sensing head 110-110' having arrays of sensing cells. The sensor units are fabricated as planar flexible integrated structures (e.g. utilizing the flexible circuit techniques) which are then folded each forming a semi-cylindrical shape of its sensor, the two sensors defining the cylindrical sensing head. The sensor cells are arranged within a circumference of the cylindrical sensing surface formed by surfaces 108 and 108' of sensors 110 and 110' respectively. This geometry is especially suited to applications requiring a tubular sensor unit (e.g. insertable into a lumen) and capable of lateral sensory. Here also, flexibility of regions 104 of signal transmission structure 120 provides for elastic movement of the sensor's head with respect to the lumen.

It should be understood that other configurations and geometries of sensor unit 100 may be employed. These include, but are not limited to, sensors configured for measuring on excision surface, cut surface, excised tissue, branched lumens, body organ contours, and skin. Also, sensor unit 100 may be provided with, but not limited to, fixed probes, hand held probes, endoscopes probes, laparoscopic probes, and robotic probes.

Reference is made to FIG. 3A showing the configuration of a near field EM sensor cell according to a specific but not limiting example. The figure shows a cross sectional view of the sensor cell 112. Cell 112 is configured as a Near field EM sensor cell 112 and defines a sensing region 114 functioning as an aperture/opening or window with respect to the EM fields (region in which the EM fields induced by the sensor cell reside/exist), an inner conductor element 118 having opposite, distal and proximal ends (with respect to the inside of the sensor unit) accommodated such that the distal end is located within sensing region 114, and an electric conductive material 116 surrounding sensing region 114 e.g. forming an electrically conductive contour/boundary at the perimeter of the sensor cell. It should be understood that generally a sensing region 114 is not limited to a planar region but rather is typically a volumetric region. The distal end of inner conductor element 118 is located within the sensing region, while not necessarily in the sensing surface, e.g. being below the sensing surface. The distal portion of the inner conductor element is surrounded by the electrically conductive contour. It should be understood that inner conductor 118 is separated from electrically conductive contour by dielectric material(s) of the sensor 110 within sensing region 114. As will be described further below, inner conductor element 118 by its opposite (proximal) end portion is electrically coupled to (e.g. physically connected with) a signal line (not shown here).

The inner conductor element 118 may be, for example, in the form of an electro-plated through-hole traversing across some layers of a multi-layer "flexible circuit" sensor. When sensor cell 112 is operated (i.e. when EM signals are transmitted to the sensor), it functions as a near field EM sensor inducing the near field EM fields within its sensing region 114, and thus in a tissue region located in the vicinity of sensing region 114. The type, extent and magnitude of the EM fields induced in said tissue region is dependent on the electrical characteristics of the tissue and on the frequency of the inducing signals. Hence, the analysis of the type, and magnitude of the EM signals induced in said tissue region provide data indicative of the characteristics of the tissue in the vicinity of the sensing region.

Figures 3E, 3F:
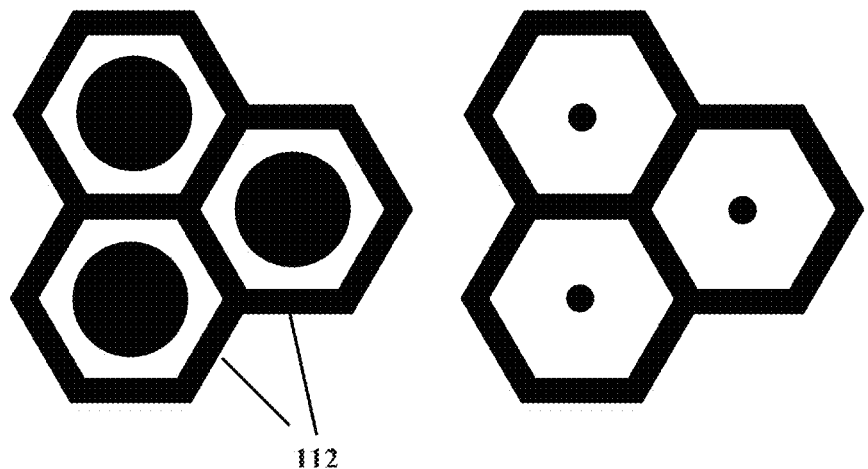
Figures 3G, 3H:
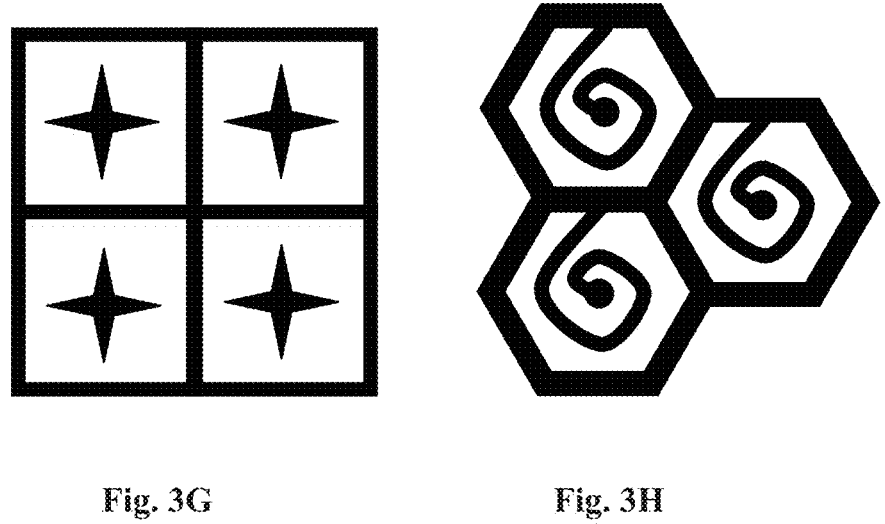
Figures 3I, 3J:
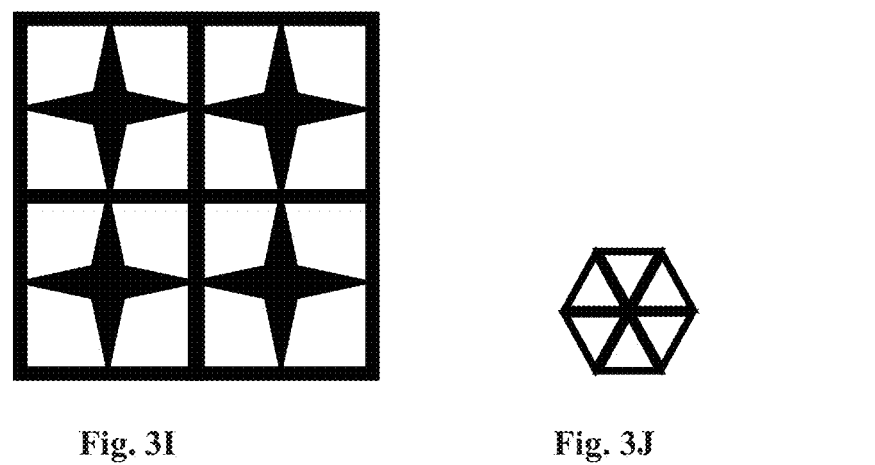

The cell contour may be of any suitable shape, e.g. hexagonal as shown in FIG. 3A and also in FIGS. 3C, 3E, 3F, 3H and 3J, as well as rectangular as shown in FIGS. 3B, 3G and 3I and triangular as shown in FIG. 3D. As further exemplified in the figures (see for example FIG. 3B-3D), the cells may be arranged such that the sensing regions form various two dimensional arrays (tiling). The cells may also be arranged as one dimensional array (not shown). Inner conductor element 118 may also be of any suitable cross sectional shape, e.g. circular (FIGS. 3A, 3E and 3F) or other shapes (FIGS. 3G to 3J).

In some embodiments of the invention, the sensor cells (or at least some of them) are configured as a resistive type EM near field sensor. Each of such resistive type sensors includes the inner conductor element 118 electrically insulated from the surrounding electrically conductive material (contour) 116. This is shown in the examples of FIGS. 3A, 3E-3G. The resistive type sensor cell may also include an electrical insulator material covering the sensing region so as to insulate the respective sensor cell from the subject, as will be described further below. Alternatively, the resistive type sensor cell may be configured to perform measurements while both the inner conductor element 118 and the surrounding electrically conductive material 116 are in direct contact with the subject, as will be described below with reference to FIGS. 4A-4C.

According to some other embodiments shown in FIGS. 3H-3J at least some of the sensor cells are configured as inductive type sensors having their inner conductor element 118 connected to the electrically conductive material 116 surrounding the respective sensing region.

Reference is made to FIGS. 4A-4D illustrating more specifically different cross-action views of a sensor unit 100 according to an embodiment of the present invention. The cross section illustrated in FIGS. 4C generally corresponds to a cut taken along a line 191 in FIG. 4A.

As shown, sensor unit includes sensor 110, defining a sensing surface 108, and signal transmission structure 120. Sensor 110 is configured as a near field EM sensor having a sensing surface 108 by which the sensor unit faces a region of interest of the subject, and an array of sensor cells 112 arranged in a spaced-apart relationship within the sensing surface. Each sensor cells 112 is configured to define a sensing region 114 surrounded by an electrically conductive material 116. The signal transmission structure 120 is flexible and is integral with sensor 110 such that they have at least one common continuous surface (layer) 127. Signal transmission structure 120 has a first layer 125 in which an array of signal connection lines 122 are located being associated with sensor cells 112 (e.g. being electrically connected/coupled to respective elements of the sensor cells, e. g., the inner conductor elements in the sensor cell configuration of the present example), and a second electrically conductive layer 126 electrically coupled to electrically conductive material 116 of the sensor. In the example presented in FIGS. 4A-4D, sensor 110 and signal transmission structure 120 have two common continuous surfaces: layer 127 and layer 126/117.

Signal transmission structure 120 defines one or more bands electrically connected to and integral with the sensor 110. In the present example, the signal transmission structure is a single-band structure 120. The signal transmission structure is configured to provide multiple signal connection lines 122 all located in a common layer 125 and associated with the plurality of sensor cells.

Figures 4A, 4B:
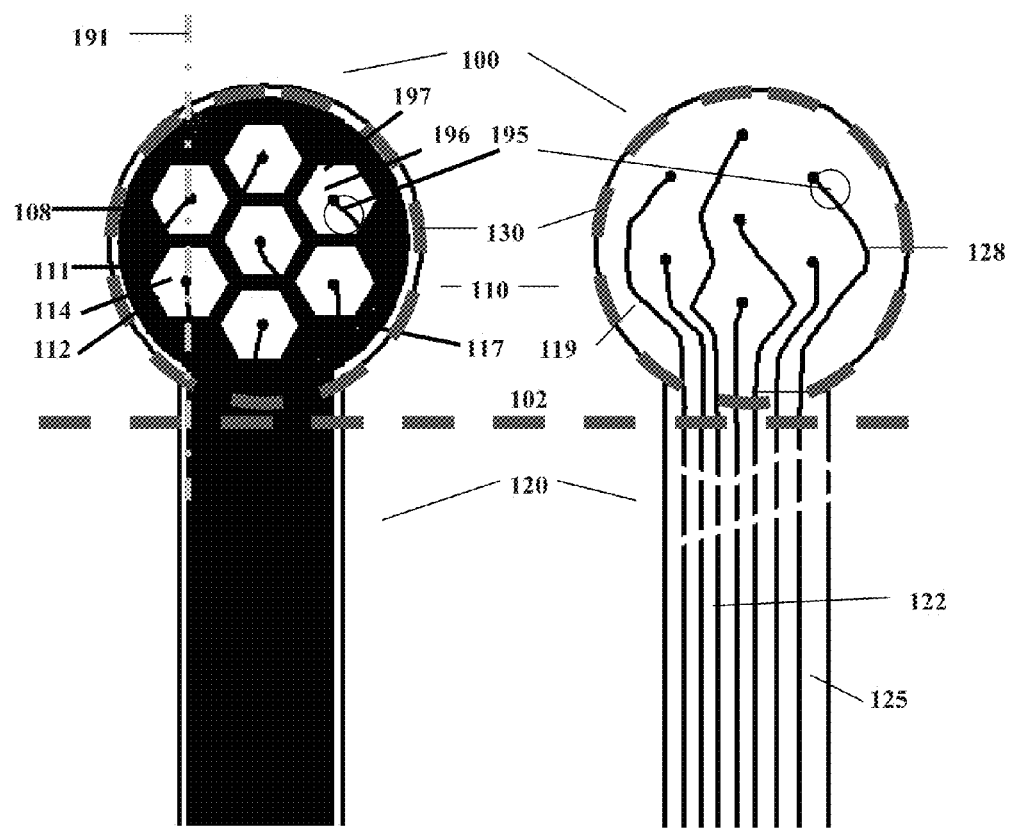
FIGS. 4A to 4C show different cross-sectional views of a sensor unit according to an example of the invention.
Figure 4C:
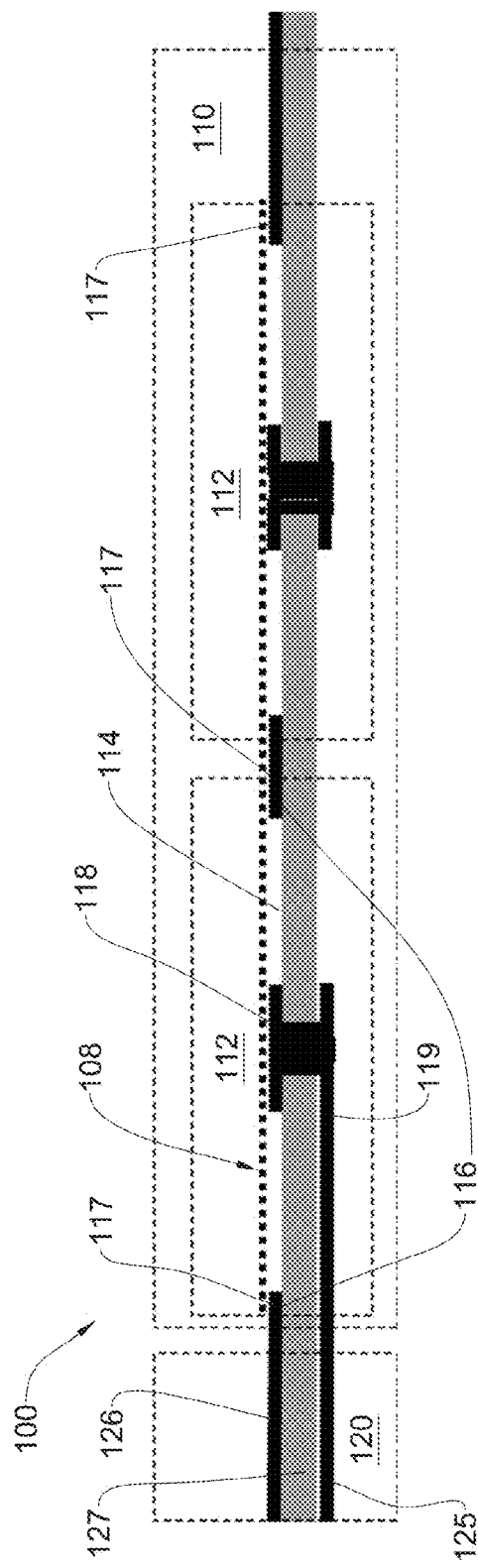

The sensor 110 includes an arrangement of signal lines electrically coupled to the signal connection lines of the signal transmission structure 120. An arrangement of such signal lines 128, feeding EM signals to array 111 of sensor cells 112, is illustrated in FIG. 4B. Also, the electrically conductive material 116 (e.g. the cells' perimeter) forms an electrically conductive layer 117 of the sensor 110 (seen in FIG. 4A) which may or may not be grounded when the sensor unit is in operation. The sensor 110 is a multi-layer structure including at least a first sensor layer 119 (including said signal lines 128) and a second conductive layer 117. Layers 119 and 117 are electrically isolated from each other (e.g. by using an electrically isolating laminate, adhesive, coating, or an additional isolation layer). In the present example, the electrical isolation is obtained by provision of an insulating (dielectric) layer 127 which serves as a substrate layer for both the layer 117 and the layer 119 of the sensor 110 and which is common also for the signal transmission structure 120.

Figure 4D:
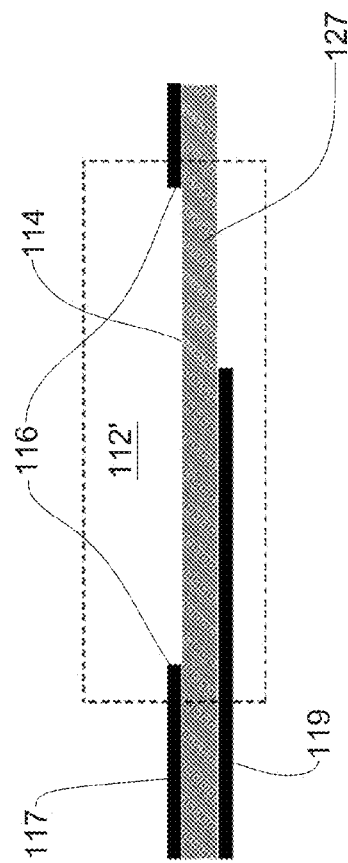
FIG. 4D exemplifies more specifically a reference sensor cell suitable to be used in the sensor unit of the invention per the embodiment of FIGS. 4A-4C.

In some embodiments of the present invention, at least one sensor cell serves as a reference cell, which electromagnetic signal is substantially not affected from the type of tissue coupled therewith, that is, when the sensor is coupled with the region of interest of the subject. For example, as shown in FIG. 4D, one of the sensor cells is a reference (e.g. dummy) cell 112', electromagnetically isolated from the medium/tissue. Such isolation can be achieved for example by a continuous conductive material coverage connecting the inner conductor element of cell 112' with its electrically conductive perimeter, or alternatively, as exemplified in FIG. 4D, by disconnecting the signal transmission line in layer 119 from the measured tissue/medium (eliminating the inner conductor element) and thus providing the desired electrical isolation between them. Such a reference cell (e.g. 112'), which is screened from an effect of the tissue portion, may serve for calibration purposes, e.g. needed because of changes in the propagation of EM signals within the flexible signal transmission structure 120 resulting from changes in the shape of signal transmission structure 120 during its movement.

Figure 4E:
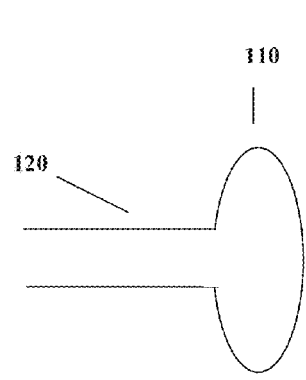
FIGS. 4E and 4F exemplify by a schematic illustration the sensor units having respectively single-band and four-band configuration of the signal transmission structure.
Figure 4F:
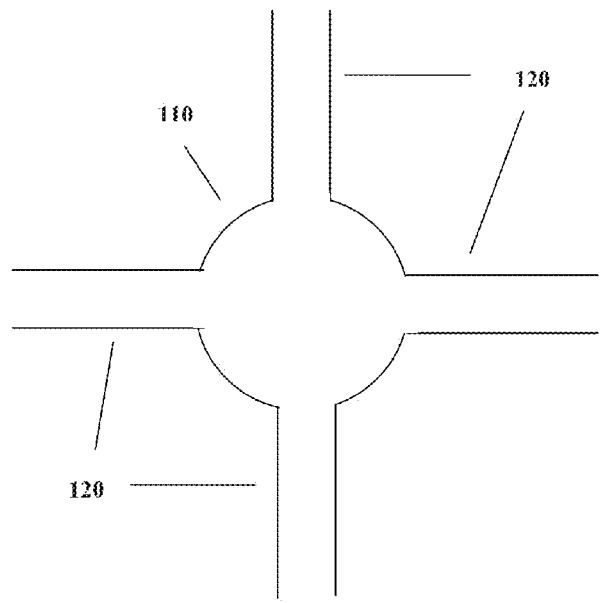

It should be understood that the invention is not limited to any specific number of bands in the signal transmission structure. Generally, there is at least one such band. As shown in FIG. 4E, as well as in the above-described examples of FIGS. 4A and 4B, the signal transmission structure 120 defines the single band. In the example of FIG. 4F, signal transmission structures 120 suitable to be used in the sensor unit has a four-band configuration. The number of such bands may vary in accordance with a specific application of the sensor unit, as well as certain factors such as the number of signal connection lines required, the minimal signal to noise ratio required and the dimensions of the sensor. This is in order to provide sufficient number of signal connection lines (e.g. in accordance with the number of sensor cells) while preserving a required spacing between the lines to maintain certain desired electrical isolation thereof and also preserving a desired flexibility (minimal bend radius) at the boundary regions 102 between the sensor unit and of the signal transmission structure. This can be achieved by utilizing multiple signal transmission bands, thus imposing minimal restrictions on the length of the sensor's perimeter 130 and therefore also on the footprint to the sensor.

As noted above, fitting the array 111 of multiple sensor cells 112 to the tip of a probe (not shown) enables spatial mapping of certain characteristics of the tissue when the sensor cells are similar, and on the other hand, when different types of sensor cells are used it enables to measure different properties in proximate regions of the tissue. It should be noted, however, that one of the prerequisites for a sensor comprising a multitude of sensor cells is to provide a number of signal connection lines 122 (i.e. in the signal transmission structure 120) electrically coupled to the sensor cells and adapted to enable readout of data (e.g. in the form of an EM signal) therefrom. Providing signal transmission structure 120 that has multitude of such signal connection lines may be especially cumbersome when the signal connection lines are required to propagate EM signals at high frequencies, for example above 1 Mhz. At such high frequencies, EM signals propagate as guided modes (or waves) along the signal connection lines (which function, together with second electrically conductive layer 126, as wave guides) and accordingly such signals may suffer from various disturbances along their path impairing their accuracy. These disturbances may include, for example, absorbance and reflectance due to various factors of the signal lines such as a change of impedance (e.g. as a consequence of changes in material and/or geometrical dimensions along their propagation path) or interference and/or crosstalk with other signals (e.g. crosstalk between different signal transmission lines) due to, for example, lack of electrical screening of signal connection lines 122, or due to proximity of signal connection lines 122 to each other.

Figure 5A:
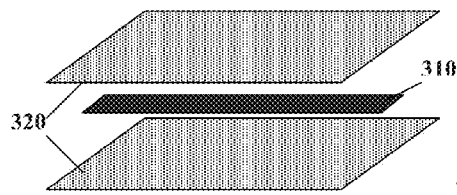
FIGS. 5A and 5B show examples of the impedance controlled signal transmission structure suitable to be used in the sensor unit of the present invention
Figure 5B:
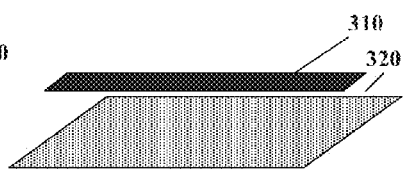

Accordingly, in order to maintain reliable and accurate signal transmission, signal transmission structure 120 carrying the EM signals to array 111 of sensor cells is impedance controlled and optionally also electrically shielded. Generally, such signal transmission structures include at least one signal line which is located with a well defined, fixed, spatial relation to at least one electrically conductive surface associated therewith and arranged in its vicinity. The signal line and electrically conductive surface are interspaced by a dielectric, non-conductive, material spacer. The spatial relation between the signal line and the conductive surface, as well as the dimensions of the signal line and the material of the dielectric spacer, determine the impedance of the line. Some examples of such impedance controlled structures are illustrated in FIGS. 5A-5B, in which a strip planar feed structure for signal transmission, or signal communication, 300A and a micro strip 300B planar feed structure are illustrated respectively. These structures comprise similar functional elements including a signal connection line 310 and one or more conductor surfaces 320 with a fixed spatial relation to the signal line. The signal line and the electrically conductive surface are interspaced by a dielectric, non-conductive, material spacer (not shown).

Conductor surfaces 320 may also provide electrical-screening (shielding) to the EM signals propagating on signal line 310. Generally the strip structure 300A provides better electrical-shielding of the signal connection line 310 since it includes two conductor surfaces 320 located from both sides of the line 310. However, for the same reason, the strip structure is generally less flexible than the micro-strip structure 300B (the minimal bend radius below which the structure breaks (or yields, or reaches fatigue), and the minimal band radius for which the structure can be elastically, or reversibly, deformed, are higher in the strip structure 300A).

According to the present invention, each one sensor cell 112 (or each bunch thereof) may be associated with a dedicated signal line (one of the lines 128) which is connected with a respective signal connection line (one of the lines 122) of the signal transmission structure 120. Lines 128 and 122 are configured for propagating EM signals therethrough and thus to and from the corresponding sensor cell(s) 112. This requires the signal transmission structure 120 to be capable of transmitting multiple EM signals (e.g. concurrently) to the sensor cells 112 and preventing spatial and/or temporal interference between these signals. At the same time, in order to provide a desirably small footprint of the sensor 110 (or sensor head), a tight bending of the signal transmission structure 120 is required at the boundary 102 between that structure 120 and the sensor 110. A bending radius should preferably be smaller (preferably, much smaller) than the dimension of the sensing surface 108, to thereby allow a small footprint of the sensor, i.e. such that the sensing surface is substantially equal to a contact area between the sensor unit and the tissue during measurements.

Alternatively (as for example in the embodiment of FIG. 2), or additionally, the flexibility of the signal transmission structure is required in order to provide a relative motion of the sensor relative to the housing of the sensor unit or relative to the signal connector structure (e.g. 160 in FIG. 1A and 1B). For example, it might be specifically important when the sensor's housing has a tubular shape (e.g. to be inserted into a lumen) and when back and forward movements of the sensor unit with respect to the housing is needed.

The above two requirements of the impedance controlled signal transmission and flexibility are achieved in the present invention by utilizing a planar (i.e. flat) signal transmission structure. It should be understood that the terms "planar" and "flat" used for the purposes of the present application actually signify a relatively thin structure at least within a region thereof where the structure can thus be bent. Also, the sensor unit of the invention has a coplanar configuration in the meaning that the sensor part and the signal transmission part are integral with one another presenting a common continuous surface.

Such a planar/flat sensor unit might have a signal transmission structure configured as a micro-strip 300B or strip structures 300A as shown in FIGS. 5A and 5B, having a controlled and fixed impedance, e.g. 50 ohm or 200 ohm.

It should also be noted that in some cases and for some types/configurations of the tissue characterization sensor cells, accurate measurements of the tissue require sufficient and preferably even coupling between the multitude of sensor cells 112 and the tissue. In this case it is preferable that also the sensor 110 is flexible and thus it is also configured as a flexible-circuit micro-strip or strip flexible structures. In other cases, however, it is preferable that the sensor 110 is rigid, and in these cases a combination of rigid sensor 110 and flexible signal transmission structure 120 can be obtained by utilizing the Rigid-Flexible circuit technology as previously described.

Signal transmission structure 120 in the examples described above includes signal layer 125 in which signal lines 122 are formed being arranged in a spaced apart relationship (having certain minimal line spacing to minimize/prevent cross-talk), and includes at least one conduction layer 126 associated with signal layer 125. As noted above, in order to provide high mechanical flexibility of signal transmission structure 120, it is preferable to minimize the number of layers in the structure 120, especially the number of conductive layers that include electrically conductive material(s), typically metals, which are typically less stretchable than insulator-materials layers. Accordingly, in preferred embodiments of the present invention the signal transmission structure 120 includes a single signal layer 125 and one or two conduction layers (only one conduction layer 126 is used in the embodiment of FIGS. 4A-4D) associated with said signal layer 125 providing impedance controlled signal transmission and optionally providing some electrical screening (shielding) to the signal lines 122.

Figure 6A:
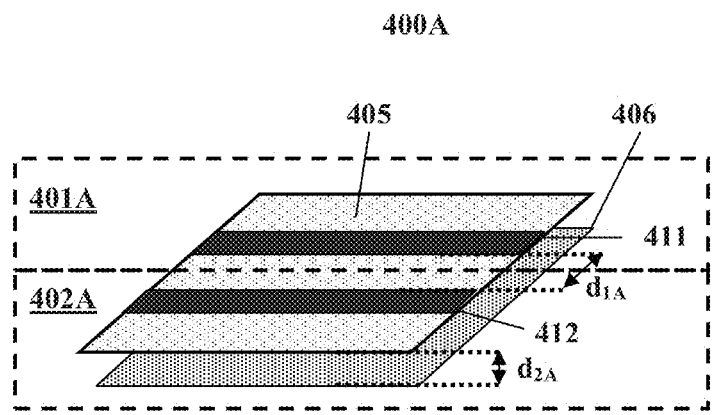
FIGS. 6A and 6B show two examples of the configuration of signal transmission bands suitable to be used in a signal transmission structure of the sensor unit according to the invention, where the example of FIG. 6B has an additional conduction layer as compared to the example of FIG. 6A.
Figure 6B:
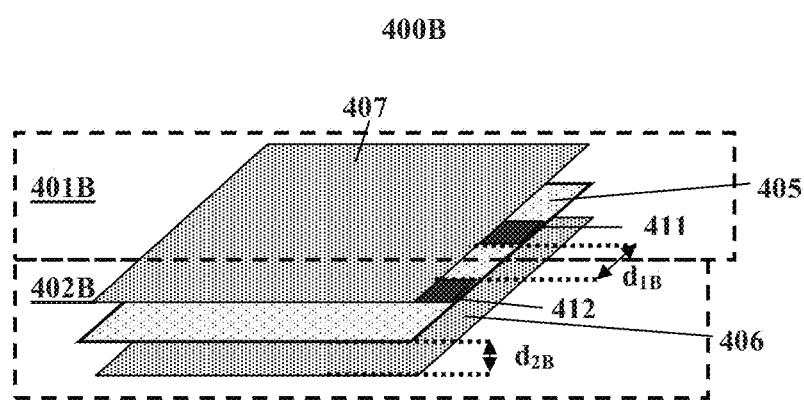

FIGS. 6A and 6B illustrate schematically two examples of signal transmission bands 400A and 400B of a signal transmission structure according to some other embodiments of the present invention. The signal transmission band 400A shown in FIG. 6A includes a first signal layer 405 that includes two spaced-apart signal lines 411 and 412, and a second conduction layer 406 that is electrically insulated from the first signal layer 405. The signal layer 405 and the second conduction layer 406 are interspaced by a dielectric, non-conductive, material spacer (not shown). Signal lines 411 and 412 and conduction layer 406 actually form a co-planar arrangement of two micro-strip feed structures 401A and 402A, in which a spacing $d_{1A}$ between the signal lines is to prevent cross-talk between signal lines 411 and 412. The spacing $d_{2A}$ between the conduction layer and signal layer, the type of dielectric spacers (not shown), and the width of the signal lines determine the impedance of the signal transmission structure. It should be understood that although in the examples of FIGS. 6A and 6B only two signal lines 411 and 412 are shown, typically more than two such signal lines are arranged within each signal transmission band.

Signal transmission band 400B shown in FIGS. 6B is generally similar to the above-described band 400A and distinguishes therefrom in that it includes an additional conduction layer 407. Signal lines 411 and 412 and conduction layers 406 and 407 are arranged, in this example, to form a co-planar arrangement of two strip feed structures 401B and 402B. Also here, spacing $d_{1B}$ between the signal lines is to prevent cross-talk between signal lines 411 and 412, and spacing $d_{2B}$ is between the conduction layers and signal layer, the type of dielectric spacers (not shown) and the width of the signal lines determine the impedance of the signal transmission structure. It should also be noted that utilizing a strip configuration as shown in FIG. 6B enables to maintain the same degree of cross talk between signal lines with a somewhat reduced spacing $d_{1B}$ between them, relative to the spacing $d_{1A}$ required by the micro-strip of FIG. 6A thus enabling to fit greater number of signal lines within a signal transmission band of the same width. On the other hand, as described above, additional conduction layer 407 and additional dielectric spacers (not shown) affect and reduce the flexibility of signal transmission band 400B. Also, when comparing between a micro-strip and a strip line configuration both having similar impedance and line width, the strip configuration requires a thicker dielectric substrate, thereby also reducing the flexibility of the signal transmission band 400B.

Thus, the type of signal transmission bands of the signal transmission structure is to be designed, inter alia, in accordance with the desired value of such parameters as the degree of allowable cross talk, the required width of the band and the number of signal lines that are to pass therethrough and the required band flexibility (e.g. the minimal possible bend radius of the transmission band that does not inflict structural damage to the band). Additionally, in some embodiments the flexibility of the signal transmission structure 120 is required in order to allow for continuous and repetitive movement of the sensor relative to the probe housing (e.g. bending of the signal transmission structure is operated at the elastic or sometimes in the elastic-plastic regions of the stress-strain curve illustrated below).

Figure 7A:
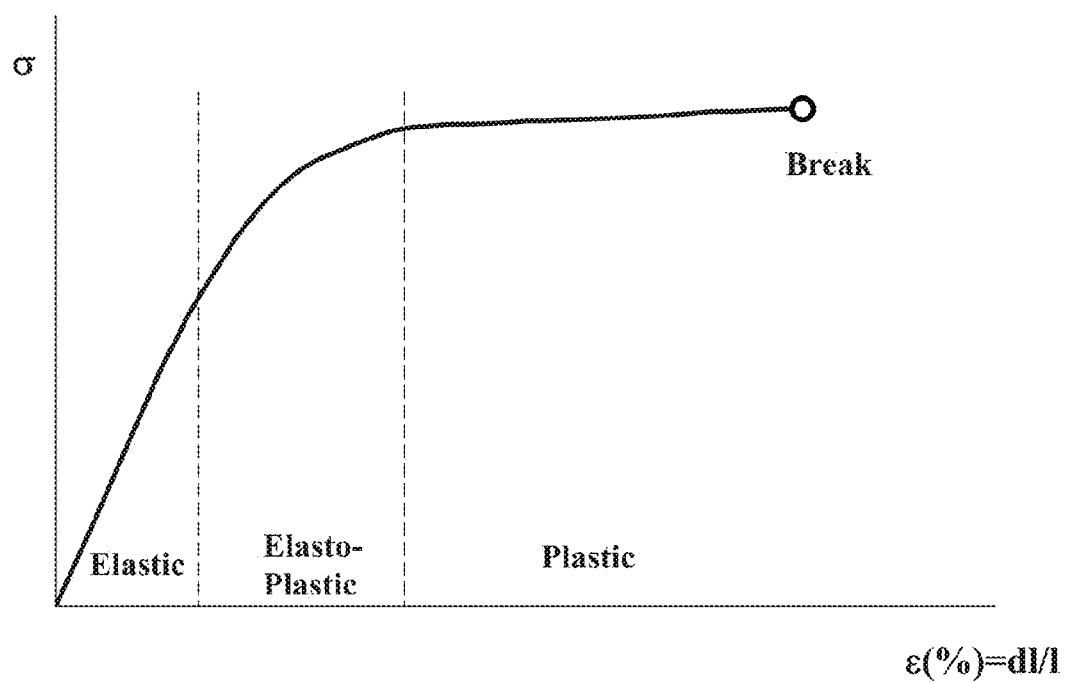
FIG. 7A shows graphically a typical stress-strain diagram of a multi layer flexible circuit structure.
Figure 7B:
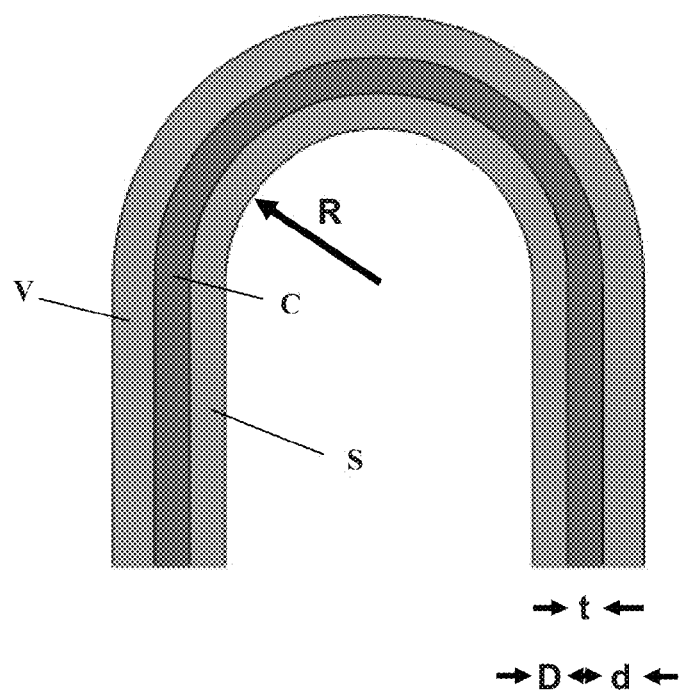
FIGS. 7B and 7C illustrate the flexibility characteristics of two examples of flexible circuit structures, having different arrangements of layers.
Figure 7C:
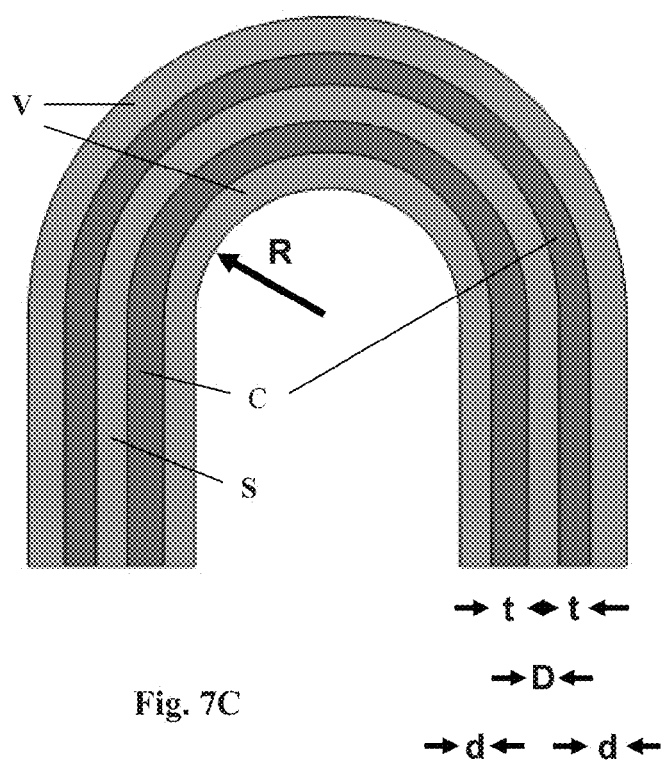

Reference is now made to FIGS. 7A-7C exemplifying the principles of selection of the appropriate layer configurations for the sensor unit in accordance with a desired flexibility/minimal bending to be obtained. FIG. 7A shows a stress-strain diagram of a typical flexible circuit. The diagram illustrates a typical Strain ε (i.e. the Change in Length l, in %) of the flexible circuit structure as a function of stress σ (i.e. Force/Area) applied to the structure, for example when the structure is being bent. As shown in the figure, the response of the structure, i.e. strain ε, to the applied force, stress σ, can be generally divided into three regimes: the elastic regime characterized by linear and reversible deformation of the structure in response to the applied force, in which the structure material returns the structure back to its original length after the application of force is released; elastic-plastic regime, which is characterized by a non-linear deformation of the structure (after the force is released, the structure material does not return the structure completely back to its original form); and plastic region characterized by linear irreversible deformation. It is thus clear that those regions of the sensor unit in which repetitive bending of the sensor unit is intended (e.g. regions 104 in FIGS. 1A, 1B and 2) minimal bent radius should be restricted to the elastic and/or elastic-plastic regimes (preferably elastic regime), while in region(s) in which a permanent bent is to be used (e.g. boundary regions 102 in FIGS. 1A and 1B) a constant/fixed minimal bent radius within the plastic regime can be utilized.

It should be noted however that these regimes may vary in accordance with the layout of the sensor unit structure (i.e. the layers thicknesses and materials). This dependence is exemplified in FIGS. 7B and 7C showing two examples of flexible circuits, having different layers structures which include one and two conductive copper layers respectively. These examples illustrate the dependence of the minimal possible bent radius on the number, material type and thicknesses of the layers in the structure within the region to be bent.

FIG. 7B illustrates a flexible circuit structure according to a specific but not limiting example. The structure includes a single substrate layer S having a thickness D=50 μm, a single copper conductive layer C having a thickness of t=35 μm and a cover layer V of a thickness d=50 μm. The maximal elongation (linear deformation) E of such structure is given by the following formula:

$$E = \frac{\frac{t}{2}}{D + \frac{t}{2} + R} \leq E_B.$$

where $E_B$ is 10% in order to avoid breakage, and $E_B$ is 0.3% when considering dynamic bending.

Accordingly, the minimal possible Bent Radius is:

$$R \geq \frac{t}{2} \cdot \frac{1-E}{E} - D$$

Hence, for the above parameters, the maximal possible deformation in the dynamic bending regime (elastic) is achieved with the minimal bend radius R≥5.766 mm, while the bend radius for which breakage will not occur is R≥0.108 mm.

FIG. 7C illustrates a flexible circuit structure according to a specific but not limiting example. The structure includes a single substrate layer S having a thickness D=50 μm and two copper conductive layers C having a thickness of t=35 μm and two cover layers V of a thickness d=50 μm arranged as shown in the figure in a self explanatory manner. Generally, the additional layers (generally thicker structure and/or multitude of conductive layers which are less flexible) limit the bending radius and thus the minimal bend radii (for dynamic and non-dynamic bending) are greater in this example as compared to that of FIG. 7B.

Here, the maximal elongation (linear deformation) E of such structure before breakage is given by the following formula:

$$E = \frac{\frac{D}{2} + t}{R + d + t + \frac{D}{2}} \leq E_B;$$

where $E_B$ is 10% in order to avoid breakage, and $E_B$ is 0.3% when considering dynamic bending.

Accordingly, the minimal possible Bending Radius is:

$$R \geq \left(\frac{D}{2} + t\right) \cdot \frac{1-E}{E} - d$$

Hence, for the above parameters, the maximal possible deformation in the dynamic bending regime (elastic) is achieved with the minimal bend radius R≥20.056 mm, while the bend radius for which breakage will not occur is R≥0.495 mm.

It should be noted that when at least one of the thickness d, D, and t is selected to be lower than those presented in the above example, the minimal bending radius can be made smaller than the value obtained in the above example. For sensing surface size of about 1-100 mm, the minimal obtainable bending radius $E_B$ is significantly smaller than the sensing surface size. The desirably small footprint of the sensor unit can thus be achieved.

Turning back to FIGS. 1A and 1B, it should be understood that the radius obtained for breakage/failure condition sets the limit for the curvature of boundary regions 102, and the radius obtained for elastic regime sets the limit for regions 104.

Referring back to FIG. 4C, sensor unit 100 is implemented as an integrated structure including a stack of three layers including substrate insulating layer 127 from both sides of which the first sensor layer 119 and the conductive layer 117 are respectively arranged. It should be understood that the substrate insulating layer 127 serves as a substrate also for the signal transmission layer 125 of the signal transmission structure 120 which is integral with first sensor layer 119 and as a substrate for the conductive layer 126 of the signal transmission structure 120 which is integral with conductive sensor layer 117. Accordingly, the signal connection lines of signal transmission layer 125 are integral with signal lines 128 of the sensor. More generally, the respective layers of the sensor 110 and the signal transmission structure 120 are arranged with one or more common continuous surfaces.

It should be noted that in the present example, the substrate layer 127 comprises Polyimide material and that copper is used as conductive material for the conductive layers 117, 126 and for the signal lines and signal connection lines of the layers 119 and 125 respectively.

Reference is made to FIGS. 8A-8D illustrating an example of a sensor unit 100 according to another embodiment of the present invention. In this example, the sensor unit includes even higher number of sensor cells than in the example of FIGS. 4A-4D thus allowing enhanced measurement resolution and allowing for a smaller minimal detectable feature size. Accordingly, a higher number of signal lines propagate through the signal transmission structure 120. To this end, the signal transmission structure 120 has two signal transmission bands 120A and 120B in which multiple signal lines traverse to different sensor cells. The division of the signal transmission structure 120 into several signal transmission bands (in this case two such transmission bands) is made in order to accommodate more signal lines within the signal transmission structure 120 without decreasing the spacing between the signal lines (thus without impairing the EM isolation of the lines) and also without increasing the footprint of the sensor 110. 15

In the embodiment shown in FIGS. 8A-8D, the sensor unit is generally similar to that of FIGS. 4A-4D. However, while in the example of FIGS. 4A-4D the sensor cells are configured to operate in direct contact with the tissue/medium, in this embodiment the sensor cells 112 are designed to operate while being electrically isolated from the inspected medium. Accordingly, an additional dielectric coating (or layer) 132 is provided, separating and electrically isolating the conductive elements 116 and 118 of the cells 112 from the inspected medium. Also in this example there is an additional dielectric layer/coating 134 covering both the first sensor layer 119 and the signal layer 125 of the signal transmission structure 120.

Figure 8C:
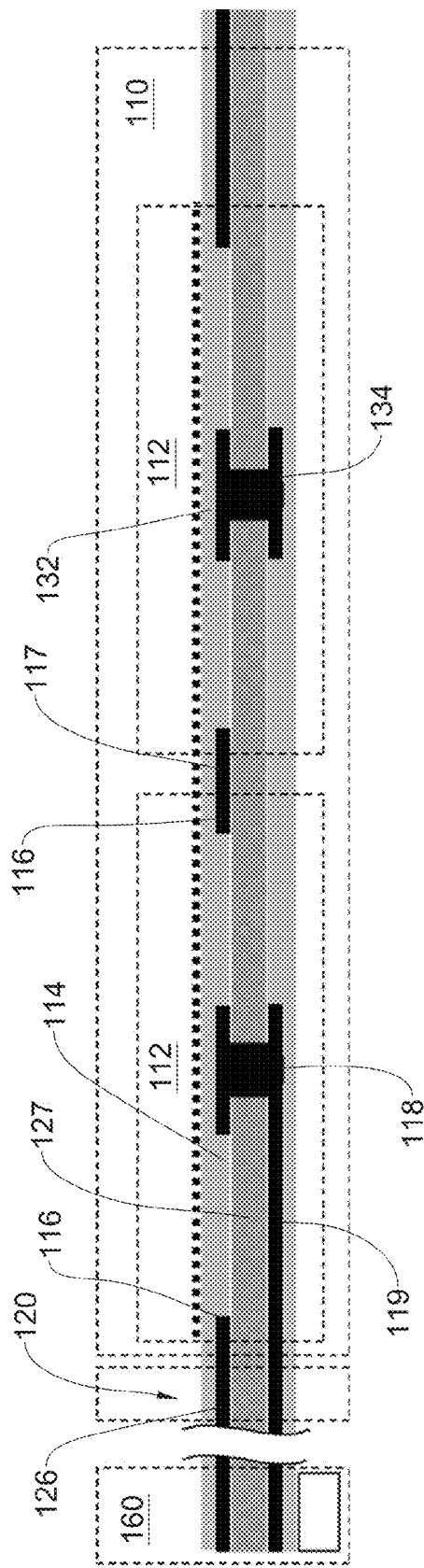
Figure 8D:
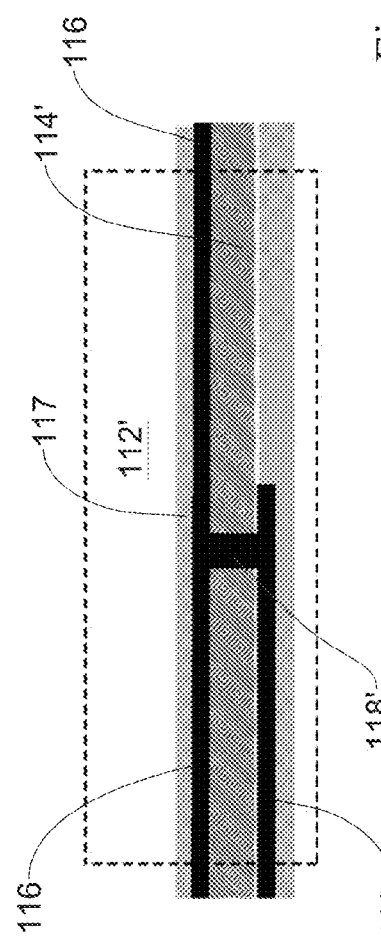
FIG. 8D exemplifies more specifically a reference sensor cell suitable to be used in the sensor unit of the invention per the embodiment of FIGS. 8A-8C.

Similarly to the embodiment of FIGS. 4A-4D, in the present example at least one sensor cell may serve as a reference cell being configured as shown in FIG. 8D. As noted above, in this embodiment the active sensor cells operate without direct electrical contact with the measured tissue and accordingly layer 132 is shown to cover the sensor cells (active cells 112 shown in the figure, but it should be understood that layer 132 also covers dummy cell 112' although in this example it is less significant). Also, in this embodiment the insensitivity of the reference cell 112' to the characteristics of the measured medium is obtained by extending the distal end of 118' to cover all the sensing area 114' and electrically coupling the inner conductor element 118' of cell 112' to with its electrically conductive perimeter 116'.

FIG. 8C also illustrates an example of the use of a rigid-flexible circuit technique in the fabrication of a sensor unit in accordance with the present invention. The layer structure of signal connector structure 160 includes a multitude of layers integral with and substantially similar to the layers of the flexible signal transmission structure 120. Rigidity of the signal connector structure 160 is provided by an additional rigidizer layer 193 which is connected to the layer structure (e.g. by suitable adhesive). It should be noted that similar techniques might be used for rigidizing other parts of the sensor unit such as the sensor's head or parts thereof and/or some regions of the signal transmission structure.

The sensor cells illustrated in the examples of FIGS. 4A-4D and 8A-8D are configured as near field EM sensors. In order to provide such sensors with good measurement accuracy, it is preferable that inner conductor element 118 located within sensing regions 114 of the sensor cell and electrically conductive material 116 surrounding the sensing regions 114 will both be located on the same sensing surface 108 (line 108 which designates the sensing surface serves only as guide to the eye and not as a structural element of the sensor) that faces the medium/tissue during measurements. To this end, inner conductor element 118 is connected to a respective signal line in the first sensor layer 119 and protrudes to the front side of the sensor towards the sensing surface 108. When the sensor cell is operated, the configuration of conductor elements comprising the distal end of inner conductor element 118 and conductive material 116 in the perimeter of the sensor cell (being in the sensing surface 108) operate together to induce the EM field in the vicinity of the tissue/medium close to sensing region 114. Typically, the inner conductor element 118, which is electrically connected to a respective signal line 128, carries an EM signal (e.g. constant voltage or alternating voltage at some frequencies), and the conductive material is held at ground potential. This affects an induction of the EM field within the tissue in close proximity to the respective sensing region of the sensor cell 112 which is the region enclosed by a perimeter of the electric conductive material 116. The penetration depth of the EM field within the tissue is typically of the order of the size of the sensing region 114 or of the order of the feature size of the distal end of inner conductor 118. The dimension of the sensing region or of the feature size of the distal end of inner conductor 118 thus defines/sets the depth to which the EM fields penetrate the medium. Selecting appropriate arrangement of the sensor cells in the sensing surface, e.g. their structure, number, size and fill factor, allows inspection a region of interest having a certain given size and located at a certain given depth in the tissue.

It should be understood that all the above considerations, when aimed at providing a flexible signal transmission structure integral with the sensor 110, create design limitations, or constraints, on the spatial arrangement/routing of signal lines within the first sensor layer 119.

It should be understood that, generally, not only the distal end (e.g. tip) of the inner conductor element 118 (e.g. the section of the inner conductor element 118 which is distal from the first sensor layer 119) induces the EM field within the tissue portion located in front of the sensing region 114, but also additional EM fields are induced within the same tissue portion by sections of the signal lines which pass within the respective sensing region 114. It should be understood that in the present disclosure, referring to signal lines passing within the sensing region designates the signal lines passing within the first (sensor's signal) layer 119 and which when projected onto the sensing surface 108 pass within the sensing region. An example of such section is illustrated in FIGS. 4A and 4B. In this example, section 195 of a signal line is passing, in the sense described above, within a sensing region/aperture 196 of sensor cell 197. The section 195 is, in this case, a part of a signal line which is associated (e.g. connected to inner conductor element of the cell) with the sensor cell 197, however it should be understood that in some cases, signal lines which pass within (or across) the aperture can be associated with other cells as well.

These additional EM fields, which are induced, as describe above, by signal lines passing within the sensing region, introduce an amount of noise to the measurement. This noise may be caused by a cross talk between the sensing region (aperture) 114 and the signal lines associated with other sensor cells passing within said sensing region 114 or by the additional near field EM fields generated in sensing region 114 by sections of signal line 119 associated with the same sensing region 114. This leads to an addition of noise (lowering the SNR) due to the non identical (from cell to cell) addition of these fields to the fields induced by distal portions of inner connectors 118 (which are identical from cell to cell).

Figure 9D:
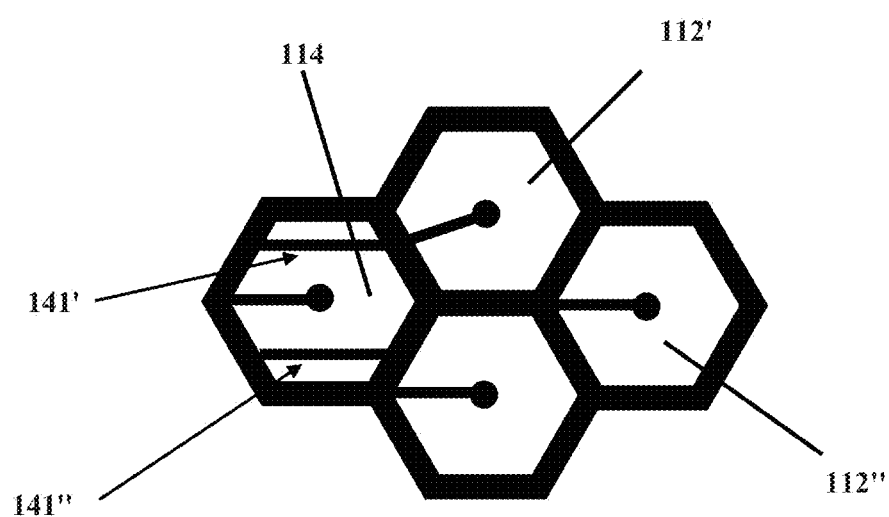

Referring now to FIG. 9A-9D, examples of a relation between the signal lines and sensing regions are more specifically shown. FIG. 9A shows first (sensor's signal) layer 119 of sensor 110 in a configuration as illustrated in FIGS. 8A-8C, FIGS. 9B and 9C show two examples of different configurations of conduction layer 117 of this sensor configuration having high fill factor (FIG. 9B) and reduced noise and crosstalk (FIG. 9C).

FIG. 9A shows that layer 119 includes multiple signal lines 128 that are associated with different sensor cells (signal lines 128 arranged to terminate within the location of their respective sensor cells). Also, signal lines 128 are shown to be integral with signal connection lines 122 of the signal transmission structure and arranged to maintain at least a certain minimal distance between the lines within the regions of both the sensor 110 and the signal transmission structure 120.

FIG. 9B illustrates an example of the sensor 110 including a conduction layer 117 placed on top of first sensor layer 119 of FIG. 9A. Layer 117 in this example includes relatively large sensing regions 114 (windows) having relatively small sized (narrow) spacing $d_s$ therebetween. Accordingly, sensing regions 114 occupy a substantial area within the sensor's sensing surface 108 thereby providing a high fill factor of the sensing regions within the sensing surface 108. FIG. 9D shows more specifically sensor cells 112, 112' and 112" and their associated signal transmission lines Generally, a high fill factor of the sensing regions in the sensing surface is desirable in order to increase the sensitivity of the sensor cell to the presence of small feature size properties of the medium under monitoring. However, configuring the sensor as herein exemplified with a high fill factor of sensing regions in the sensing surface might either impair the sensor's accuracy or allow the use of only a small number of sensor cells thus reducing the applicable resolution of the sensor. This is because the narrow spaces $d_s$ allow only a limited number of signal lines to traverse between the sensing regions while being electrically shielded therefrom. This is also because a certain minimal spacing between the signal lines has to be maintained in accordance with a desired degree of electric isolation between adjacent signal lines (e.g. to prevent cross talk), so that the signal lines cannot be all made to accommodate only the regions $d_s$. Hence, in the case of high spatial resolution requirement which in turn requires a greater number of signal lines, the signal lines of different sensor cells would unavoidable pass through the sensing regions of other sensor cells. For example, the portions of signal lines 141' and 141" associated with cells 112' and 112" pass through the sensing aperture 114 of another sensor cell 112. As described above, these signal lines induce additional EM fields within the tissue portion to which the sensing region 114 is coupled and thus impair the accuracy of the measurements and affect crosstalk between the different sensor cells. Also, since the size of the sensing region in this example is relatively large, the portion of the signal line that is associated with a respective sensor cell and which pass through the cell's sensing region 114 is also quite lengthy, thus also impairing the accuracy of the measurement of the sensor cell.

Moreover, as noted above, during operation the sensor cell actually integrates the EM response of a tissue region located in front of its respective sensing aperture. The EM response of said tissue regions corresponds to the spatial distribution of the EM fields generated within the sensing aperture of the sensor cells. Different types of sensor cells (for example such as those illustrated in FIGS. 3E-3J) are designed to induce different spatial configurations of EM fields having for example circular, rectangular, hexagonal symmetries. The analysis of the tissue characteristics is largely dependent on the spatial configuration of the induced fields which in turn might be susceptible to electrical interferences such as those induced by the sections of the signal lines passing within the sensing region, for example as described above, sections 141', 141" (see also FIG. 9D). Hence avoiding/reducing such effects of electric interferences by electrically screening the sections of the signal lines passing within the aperture and the section of the inner conductor element, other than its distal end, from the sensing regions of the sensor cells, provide tissue characterization measurements with improved accuracy.

FIG. 9C illustrates another example of the sensor 110 including conduction layer 117 placed on top of the first sensor layer 119 of FIG. 9A. Here, layer 117 includes relatively small sensing regions 114 arranged with relatively large (broad) spacing $d_s$ between them, and accordingly the portions of signal lines that traverse or pass within the sensing regions are small and the cross talk between the sensor cells is minimized In this example the sensing regions 114 occupy a relatively small area of the sensor's sensing surface 108 thus providing lower fill factor of the sensing regions.

Figure 10A:
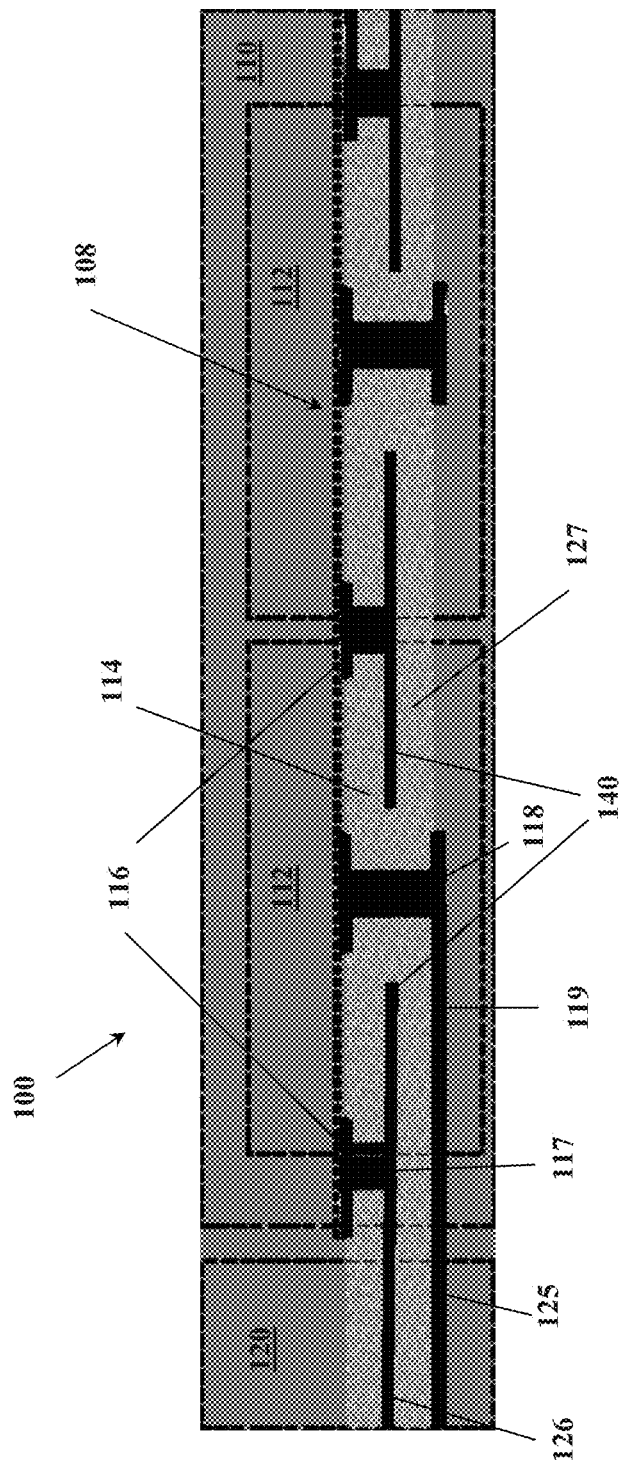
FIG. 10A shows a side cross-sectional view of a sensor unit according to another embodiment of the present invention, configured to enable high signal to noise ratio and high spatial resolution and/or high fill factor.

The invention allows for providing a high spatial resolution sensor unit that has relatively high signal to noise ratio (e.g. crosstalk between the different sensor cells is suppressed) and has relatively high fill factor of sensing regions. In this connection, reference is made to FIG. 10A showing a side cross-sectional view of a sensor unit according to another embodiment of the present invention. The sensor unit is configured generally similar to that of FIGS. 4A-4C and 8A-8C. More specifically, the sensor unit includes a sensor 110 and a signal transmission structure 120 integral with the sensor 110, both having common continuous surface 127. Sensor 110 includes an array 111 of sensor cells (e.g. 112) which define a respective array of sensing regions (e.g. 114) surrounded by electrically conductive material 116. Sensor 110 includes a first sensor layer 119 containing signal lines 128 and a second conduction layer 117 in which the sensing regions are made (e.g. in the form of electrically insulating windows or perforations) and which include the electrically conductive material 116 surrounding the sensing regions. The sensor cell also includes an inner conductor element 118 protruding from the first sensor layer 119 towards the sensing surface 108. In order to obtain high signal to noise ratio, as well as high spatial resolution and/or high fill factor, the portions of the signal lines that pass within the sensing regions should be electrically shielded (screened) from the sensing regions 114 themselves. In the present example of FIG. 10A, this is achieved by utilizing an additional conductive layer 140 located in between the first sensor layer 119 carrying the signal lines and the second conductive layer 117 in which the sensing regions are made. The additional conductive layer 140 acts as an electrical shield, screening signal lines that traverse in the first sensor layer 119, passing within the sensing regions, from the sensing regions, and thus from the sensing surface 108.

Figure 10B:
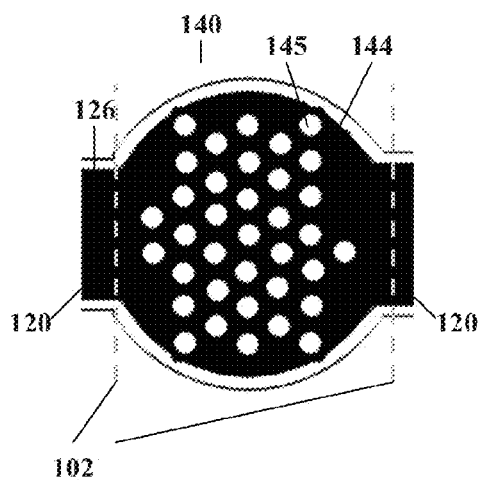
FIGS. 10B and 10C more specifically illustrate two different examples of the layers' structure in the sensor part of the sensor unit.

An example of the configuration of the additional layer 140 is shown more specifically in FIG. 10B. Layer 140 is a conductive layer that includes an array 144 of signal transmission regions 145 (e.g. in the form of perforations in layer 140), which are substantially non-conductive regions and are arranged in a spaced apart relationship in layer 140 being aligned with at least some of the sensing regions. In other words, the array 144 of signal transmission regions 145 corresponds to the array of the sensing regions associated with the sensor cells array 111. It should be noted that transmission regions 145 may be concentric with the sensing regions 114 and be generally smaller than the sensing regions 114 thereby providing by said additional conductive sensor layer an electrical screening of at least a portion of the signal lines from the sensing regions. Here the additional layer is integral with the conductive layer 126 of the signal transmission structure 120 (only small portion of which is shown).

Figure 10C:
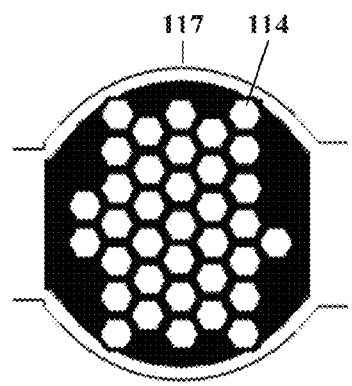

FIG. 10C illustrates schematically the conduction layer 117 including an array 130 of sensing regions 114. It should be understood that in the assembled sensor configuration the conduction layer 117 is located above the additional layer 140 and faces the tissue/medium to be characterized. Transmission regions 145 provide access to the inner conductor elements of the sensor cells while electromagnetically screening other portions of the signal transmission layer, those passing within the sensing regions 114.

The arrangement presented in FIGS. 10A-10C leads to that the structure of the induced EM near field in the sensing region 114 of each of the sensor cells 112 will not be affected by sections of signal lines passing within the sensing regions 114. This leads to an increase in the SNR of the measurements, and thus to an increase in the characterization capabilities of sensor 110.

It should be noted that also in this example the sensor unit is implemented as an integrated structure including a stack of layers. However, in contrary to the previous examples presented, here the conductive layer 126 of the signal transmission structure 120 is integral with the additional sensor layer 140. In this connection it should be noted that in this example, in order to provide high flexibility of the boundary 102 between the senor 110 and the signal transmission structure, the additional layer extends only within the region of the sensor 110 (e.g. not extending through boundary 102 to the signal transmission structure 120).

Those skilled in the art will readily appreciate that various modifications and changes can be applied to the embodiments of the invention as hereinbefore described without departing from tic scope defined in and by the appended claims.

The invention claimed is:

1. A sensing device for use in measurements in a body cavity of a subject, the sensing device comprising a housing carrying a sensing head and one or more near-field electromagnetic (EM) tissue characterization sensor units, the sensing head being formed by respective one or more sensing surfaces of said one or more near-field EM sensor units, wherein each sensing surface comprises an electrically conductive material formed as a flat layer by which the sensing head faces a region of interest in the body cavity, each near-field EM sensor unit further comprises:

an array of sensor cells defining a corresponding array of sensing regions arranged in a spaced-apart relationship in said sensing surface and surrounded by said electrically conductive material, and a flexible signal transmission structure integral with said sensing surface such that the signal transmission structure and the sensing surface have at least one common continuous surface, said signal transmission structure comprises a first layer comprising an array of spaced-apart signal connection lines associated respectively with said array of sensor cells and a second layer being electrically conductive and electrically coupled to said flat layer of the sensing surface;

the near-field EM sensor units being configured for providing impedance controlled signal transmission to and from the sensing regions.

2. The sensing device of claim 1, wherein said housing is flexible.

3. The sensing device of claim 1, wherein said body cavity comprises one of the following: lumens, branched lumens, organ contour and excision surfaces.

4. The sensing device of claim 1, wherein the one or more sensing surfaces is or are substantially planar or curved surfaces.

5. The sensing device of claim 1, wherein the sensing head comprises at least two of said one or more near-field EM sensor units, the sensing head being a substantially cylindrical surface formed by the sensing surfaces of said at least two of said one or more near-field EM sensor units, the sensing regions of said at least two of said one or more near-field EM sensor units being arranged in a spaced-apart relationship within a circumference of said cylindrical surface.

6. The sensing device of claim 1, wherein the housing has a tubular-like configuration.

7. The sensing device of claim 1, wherein each of said one or more near-field EM sensor units carried by said housing is capable of lateral sensory.

8. The sensing device of claim 1, wherein said flexible signal transmitting structure has at least one flexible band configured for bending with respect to the sensing surface with a radius of curvature smaller than a characteristic dimension of said sensing surface.

9. The sensing device of claim 1, wherein said signal transmission structure has one of the following configurations: (a) is configured as a flexible planar microstrip having a plurality of layers including said first and second layers being flexible planar layers; (b) is configured as a flexible planar strip comprising a plurality of layers including the first and second layers, and additional electrically conductive layer, the second and the additional layers being located at both sides of said first layer.

10. The sensing device of claim 1, wherein the sensing surface of the near-field electromagnetic sensor unit is flexible.

11. A laparoscopic device comprising the sensing device of claim 1.

12. The sensing device of claim 1, wherein one or more of said one or more near-field EM sensor units are adapted for relative motion with respect to the housing.

13. The sensing device of claim 12, wherein each of said one or more near-field EM sensor units is mounted for back and forward motion relative to the housing.

14. The sensing device of claim 1, wherein each of at least some of said sensor cells of said one or more near-field EM sensor units comprises an inner conductor element coupled to inside of the respective sensing region and electrically coupled to the respective one of said signal connection lines.

15. The sensing device of claim 14, wherein at least some of the sensor cells are configured as a resistive type sensor, each of said resistive type sensors has one of the following configurations: (i) the inner conductor element of the resistive type sensor is electrically insulated from the surrounding electrically conductive material; (ii) the sensor cell of the resistive type sensor comprises an electrical insulator material covering the sensing region and insulating said sensor cell from the subject; (iii) the resistive type sensor cell is configured to perform measurement, while the inner conductor element and the surrounding electrically conductive material are brought in direct contact with the subject.

16. The sensing device of claim 14, wherein at least some of the sensor cells are configured as inductive type sensors, the inner conductor element of each of the inductive type sensor cells being connected to the electrically conductive material surrounding the respective sensing region.

17. The sensing device of claim 1, wherein the near-field electromagnetic sensor unit comprises: a first sensor layer comprising a plurality of signal lines, which are electrically coupled to said signal connection lines of the signal transmission structure and which are thus associated with the corresponding sensor cells; and a second sensor layer comprising said electrically conductive material and defining said sensing surface, said second sensor layer being electrically coupled to the second electrically conductive layer of the signal transmission structure.

18. The sensing device of claim 17, wherein said near field electromagnetic sensor unit comprises an additional sensor layer being electrically conductive and located in between said first and second sensor layers; said additional sensor layer having spaced-apart signal transmission regions configured as substantially non-conductive regions aligned with at least some of the sensing regions, said signal transmission regions being substantially smaller than the corresponding sensing regions, thereby providing by said additional sensor layer an electrical screening of at least a portion of the signal lines from the sensing regions.

19. An endoscope comprising the sensing device of claim 1.

20. The endoscope of claim 19, wherein said sensing head is mounted on the housing such that each of the one or more near-field EM sensor units is movable with respect to the housing.

21. A sensing device for use in measurements in a body cavity of a subject, the sensing device comprising a housing carrying a sensing head and one or more near-field electromagnetic (EM) tissue characterization sensor units, the sensing head being formed by respective one or more sensing surfaces of said one or more near-field EM sensor units, wherein
each near-field EM sensor unit further comprises:
an array of sensor cells defining a corresponding array of sensing regions arranged in a spaced-apart relationship in said sensing surface and surrounded by said electrically conductive material, and
a flexible signal transmission structure integral with said sensing surface such that the signal transmission structure and the sensing surface have at least one common continuous surface,
the near-field EM sensor units being configured for providing impedance controlled signal transmission to and from the sensing regions,
wherein said near field electromagnetic sensor unit comprises an additional sensor layer being electrically conductive and located in between said first and second sensor layers; said additional sensor layer having spaced-apart signal transmission regions configured as substantially non-conductive regions aligned with at least some of the sensing regions, said signal transmission regions being substantially smaller than the corresponding sensing regions, thereby providing by said additional sensor layer an electrical screening of at least a portion of the signal lines from the sensing regions.

* * * * *